(12) United States Patent
Ashley et al.

(10) Patent No.: US 8,946,405 B2
(45) Date of Patent: *Feb. 3, 2015

(54) CONTROLLED RELEASE FROM SOLID SUPPORTS

(75) Inventors: Gary Ashley, Alameda, CA (US); Daniel V. Santi, San Francisco, CA (US)

(73) Assignee: Prolynx LLC, San Francisco, CA (US)

( * ) Notice: Subject to any disclaimer, the term of this patent is extended or adjusted under 35 U.S.C. 154(b) by 173 days.

This patent is subject to a terminal disclaimer.

(21) Appl. No.: 13/696,300

(22) PCT Filed: May 5, 2011

(86) PCT No.: PCT/US2011/035422
§ 371 (c)(1),
(2), (4) Date: Jan. 28, 2013

(87) PCT Pub. No.: WO2011/140392
PCT Pub. Date: Nov. 10, 2011

(65) Prior Publication Data
US 2013/0123487 A1    May 16, 2013

Related U.S. Application Data

(60) Provisional application No. 61/331,742, filed on May 5, 2010.

(51) Int. Cl.
| | | |
|---|---|---|
| A61K 47/48 | (2006.01) | |
| A61K 49/00 | (2006.01) | |
| A61L 15/44 | (2006.01) | |
| A61L 27/54 | (2006.01) | |
| A61L 29/16 | (2006.01) | |
| A61L 31/16 | (2006.01) | |

(52) U.S. Cl.
CPC ..... *A61K 47/48215* (2013.01); *A61K 47/48176* (2013.01); *A61K 47/48292* (2013.01); *A61K 47/48784* (2013.01); *A61K 47/48976* (2013.01); *A61K 47/48992* (2013.01); *A61K 49/0043* (2013.01); *A61K 49/0054* (2013.01); *A61L 15/44* (2013.01); *A61L 27/54* (2013.01); *A61L 29/16* (2013.01); *A61L 31/16* (2013.01); *A61K 47/48023* (2013.01); *A61K 47/4823* (2013.01); *A61L 2300/252* (2013.01); *A61L 2300/258* (2013.01)
USPC .......................................................... 536/53

(58) Field of Classification Search
CPC ................. A61K 47/48215; A61K 47/48023; A61K 47/4823
USPC .......................................................... 536/53
See application file for complete search history.

(56) References Cited

U.S. PATENT DOCUMENTS

| | | | |
|---|---|---|---|
| 7,229,473 B2 | 6/2007 | Falotico et al. | |
| 7,585,837 B2 | 9/2009 | Shechter et al. | |
| 7,647,099 B2 | 1/2010 | Marchitto et al. | |
| 8,703,907 B2 * | 4/2014 | Ashley et al. | 530/308 |
| 8,754,190 B2 * | 6/2014 | Ashley et al. | 530/331 |
| 2003/0190341 A1 | 10/2003 | Shalaby et al. | |
| 2010/0029646 A1 | 2/2010 | Christensen et al. | |

FOREIGN PATENT DOCUMENTS

| | | |
|---|---|---|
| WO | WO-01/92584 | 12/2001 |
| WO | WO-2009/055637 | 4/2009 |
| WO | WO-2009/158668 | 12/2009 |

OTHER PUBLICATIONS

Supplementary European Search Report for EP 11778383.7, mailed Oct. 10, 2013, 6 pages.
International Search Report for PCT/US2011/035422, mailed Jul. 29, 2011, 1 page.

* cited by examiner

*Primary Examiner* — Brandon Fetterolf
*Assistant Examiner* — Yih-Horng Shiao
(74) *Attorney, Agent, or Firm* — Morrison & Foerster LLP

(57) ABSTRACT

The invention relates to solid supports useful in medical applications that provide controlled release of drugs, such as peptides, nucleic acids and small molecules. The drugs are covalently coupled to the solid support through a linkage that releases the drug or a prodrug through controlled beta elimination.

16 Claims, 3 Drawing Sheets

Linear free energy relationship of the half-lives for release of H-Lys(DNP)-OH from substituted (phenylsulfonyl)ethyl linked carbamates.

Linear free energy correlation between rate of H-Lys(DNP)-OH release where, $R^2 = -(CH_2)_3C\equiv CH$ at 25°C from compounds of Figure 5 and the Hammett $\sigma_p$; left to right, $R^1 = $ -OMe, -CH$_3$, -H, -Cl

CONTROLLED RELEASE FROM SOLID SUPPORTS

CROSS-REFERENCE TO RELATED APPLICATION

This application is the national phase of PCT application PCT/US2011/035422 having an international filing date of 5 May 2011, which claims benefit under 35 U.S.C. §119(e) to provisional application 61/331,742 filed 5 May 2010. The contents of the above patent applications are incorporated by reference herein in their entirety.

TECHNICAL FIELD

The invention relates to medical devices and other pharmacologically useful solid supports that are covalently bond to a multiplicity of drug molecules through covalent linkers that release drug through controlled beta elimination reactions.

BACKGROUND ART

There is a plethora of approaches to arranging for controlled release of drugs or growth factors useful in medicine from solid supports. For example, stents that are coated with polymers that contain drugs and release them over time are disclosed in U.S. Pat. No. 7,229,473, representative of a large number of disclosures of such approaches. Devices that release drugs at a controlled rate are described in U.S. Pat. No. 7,647,099. In general, however, the drugs or growth factors used in these approaches are noncovalently contained within the polymeric matrix.

More recently, compositions and methods have been described for controlled release of drugs covalently coupled to macromolecules, such as polyethylene glycol (PEG), in order to enhance pharmaceutical properties, such as half-life, stability, solubility, tolerability, and safety. In one method, drug moieties are coupled to macromolecules through a permanent linker, but this approach is limited by at least two factor: 1) the linker must be attached to the drug moiety at a site that does not hinder biological activity, and 2) permanent conjugates generally cannot cross the cell membrane, so the approach may only be feasible for extracellular drug targets. In a second approach, covalently bound drug-macromolecule conjugates employ PEG as a releasable carrier of the drug or prodrug. Typically, the drug is attached to the carrier by an ester or carbonate linkage that can be cleaved by esterase-catalyzed hydrolysis. Examples are PEG-camptothecin, PEG-SN38, PEG-irinotecan and PEG-docetaxel. Additional adaptations have been made to accommodate amine-containing drugs whereby a PEG moiety is connected by a cleavable ester to a self-immolating carbamate. This technology has been applied to peptides and proteins as well as to daunorubicin, amphotericin, Ara-C and other small molecules. However, drug release rates in these cases is unpredictable and difficult to adjust, because esterase activity varies between species and individuals, and certain compartments are esterase-deficient (e.g., topical, intra-ocular, interstitial areas).

Researches at the Weizmann Institute developed a system in which a protein or polymer carrier is attached to linkers such as fluorenylmethoxycarbonyl (Fmoc) or its 2-sulfo derivative (Fms). These are described in U.S. Pat. No. 7,585,837. These linkers release drugs via a non-enzymatic beta-elimination mechanism; however, tunable control over the release rate remains a problem with this system.

PCT publication WO2009/158668 describes drug-macromolecule conjugates wherein the drug is released through a beta-elimination mechanism, and wherein the rate of beta-elimination is controlled by a trigger independent of the macromolecule itself. This solves a problem left unsolved in the prior art. The release mechanism set forth in the '668 PCT publication has not been applied to instances where a multiplicity of drugs is coupled covalently, but releasably, to the surface of or interstices of solid supports.

The present invention provides for drug-solid support conjugates wherein the drug is released at a controlled rate from the solid support. In addition to providing a controllable rate of release of the drug from the solid support itself, this approach offers a means whereby the coupled drug is protected from hydrolysis by the presence of a protective polymer, such as PEG, on different sites at the surface or interstices of the solid support.

DISCLOSURE OF THE INVENTION

The invention provides conjugates of drugs, growth factors, or other biological agents such as viral delivery agents, with solid supports that are useful in physiology and medicine, comprising cleavable linkers that allow for subsequent release of the drugs at controlled rates under physiological conditions, as well as solid supports comprising the cleavable linkers, synthetic intermediates, and methods for the preparation and use of the above. In general, a linker is covalently bound to multiple sites on the solid support, and each linker is in turn coupled to an appropriate drug or prodrug. The drug or prodrug is then released at the desired rate through a beta-elimination reaction at physiological pH. In addition, the drug sites on the support may be contained within a protective layer of polymer bound to adjacent sites on the solid support.

Thus, in one aspect, the invention is directed to a composition of the formula

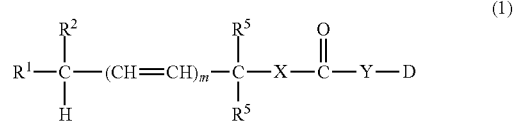

(1)

wherein
m is 0 or 1;
at least one or both $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
   $R^3$ is H or optionally substituted alkyl;
   aryl or arylalkyl, each optionally substituted;
   heteroaryl or heteroarylalkyl, each optionally substituted; or
   $OR^9$ or $N(R^9)_2$ wherein each $R^9$ is independently H or optionally substituted alkyl, or both $R^9$ groups taken together with the nitrogen to which they are attached form a heterocyclic ring;
$SR^4$ wherein
   $R^4$ is optionally substituted alkyl;
   aryl or arylalkyl, each optionally substituted; or
   heteroaryl or heteroarylalkyl, each optionally substituted;

wherein $R^1$ and $R^2$ may be joined to form a 3-8 membered ring; and wherein one and only one of $R^1$ and $R^2$ may be H or may be alkyl, arylalkyl or heteroarylalkyl, each optionally substituted;

each $R^5$ is independently H or is alkyl, alkenylalkyl, alkynylalkyl, aryl, arylalkyl, heteroaryl or heteroarylalkyl, each optionally substituted;

D is a residue of a drug or prodrug coupled through O, S, or N;

Y is absent and X is O or S; or

Y is $NBCH_2$ and X is O;

wherein B is alkyl, aryl, arylalkyl, heteroaryl or heteroarylalkyl, each optionally substituted; and wherein one of $R^1$, $R^2$, $R^5$ or B is coupled to a solid support.

Said solid support may also be further coupled to a protective inert polymer.

Alternatively phrased, the invention is directed to a solid support coupled to a multiplicity of substituents of the formula

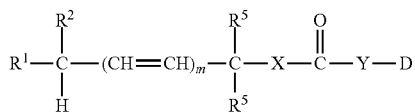

(2)

wherein m is 0 or 1;

at least one or both $R^1$ and $R^2$ is independently CN; $NO_2$; optionally substituted aryl;

optionally substituted heteroaryl;

optionally substituted alkenyl;

optionally substituted alkynyl;

$COR^3$ or $SOR^3$ or $SO_2R^3$ wherein
   $R^3$ is H or optionally substituted alkyl;
   aryl or arylalkyl, each optionally substituted;
   heteroaryl or heteroarylalkyl, each optionally substituted; or
   $OR^9$ or $N(R^9)_2$ wherein each $R^9$ is independently H or optionally substituted alkyl, or both $R^9$ groups taken together with the nitrogen to which they are attached form a heterocyclic ring;

$SR^4$ wherein
   $R^4$ is optionally substituted alkyl;
   aryl or arylalkyl, each optionally substituted; or
   heteroaryl or heteroarylalkyl, each optionally substituted;

wherein $R^1$ and $R^2$ may be joined to form a 3-8 membered ring; and wherein one and only one of $R^1$ and $R^2$ may be H or may be alkyl, arylalkyl or heteroarylalkyl, each optionally substituted;

each $R^5$ is independently H or is alkyl, alkenylalkyl, alkynylalkyl, aryl, arylalkyl, heteroaryl or heteroarylalkyl, each optionally substituted;

D is a residue of a drug or prodrug coupled through O, S, or N;

Y is absent and X is O or S; or

Y is $NBCH_2$ and X is O;

wherein B is alkyl, aryl, arylalkyl, heteroaryl or heteroarylalkyl, each optionally substituted; and wherein said coupling is through one of $R^1$, $R^2$, $R^5$ or B.

The solid support may also comprise a multiplicity of protective inert polymers, such as PEG. The solid support may be, for example, a stent, a hydrogel, a catheter, a wound dressing, an implant, a plaster, an orthopedic device, or a dental prosthesis.

In other aspects, the invention is directed to methods to prepare the compositions of the invention, and methods to employ them in medical/veterinary/physiological procedures. It also includes intermediates in the synthesis of formulas (1) and (2).

Thus, the invention further includes "precursor" molecules identical to formula (1) or (2) in which one of $R^1$, $R^2$, $R^5$ or B is coupled to the solid support, except that in lieu of a drug or prodrug residue a leaving group is present. The solid support thus has substituents of formula (3)

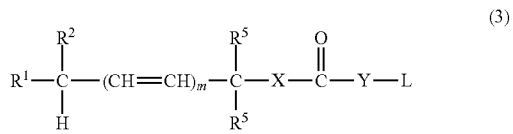

(3)

wherein $R^1$, $R^2$, $R^5$, X, Y and m are as defined as in formula (1) or (2); and wherein L is a nucleofuge for coupling the drug or prodrug to the remainder of the molecule.

In a further aspect, the present invention provides for a drug-solid support conjugate, wherein the drug is connected to the solid support via a linker, the drug molecule is attached to the linker through an O, S, or N, and wherein the drug is released from the conjugate under physiological conditions through a beta-elimination reaction.

In a still further aspect, the present invention provides for compounds of formula (4)

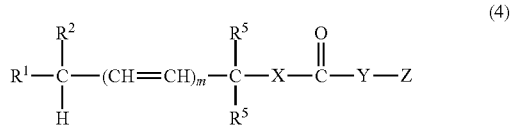

(4)

wherein Z is D or L; $R^1$, $R^2$, m, $R^5$, X, Y, D, and L are as defined above, but rather an being coupled to a solid support, one of the $R^1$, $R^2$, $R^5$ and B groups comprises a functional group allowing for coupling to a solid support.

DESCRIPTION OF THE INVENTION

Nature of the Solid Support

Figure 1:
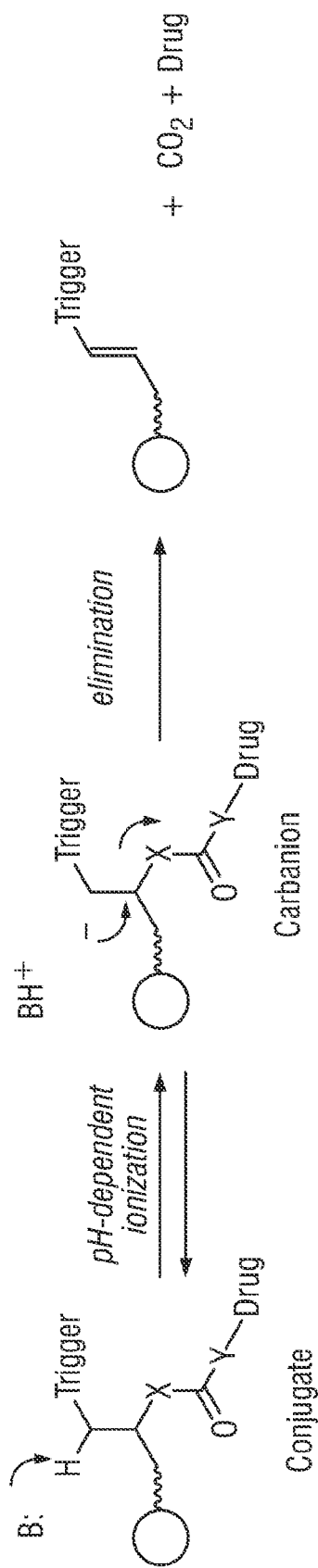
FIG. 1 shows the general nature of release of drug or prodrug by β-elimination.

There are many situations where it is desirable to provide a drug at a predetermined rate in situ at a specified location. In the most general sense, a solid support which provides a controlled release of such a drug (or prodrug) may be termed an "implant" or a "topical applicator." Such implants and topical applicators may take many forms, including vascular grafts and neural probes.

For instance, one of the most common instances of an "implant" that serves both a mechanical purpose and a drug dispensing purpose is an intravascular stent. Such stents may be metallic or polymeric and in many instances are designed to release drugs that have been noncovalently entrapped in a polymeric coating. Antiproliferative agents which are helpful in preventing restenosis may be included as well as thromboxane inhibitors angiotensin converting enzyme inhibitors, and prostacyclin mimetics. According to the present invention, such drugs may be covalently coupled to either polymeric or metallic stents using the linkers and methods of the invention.

Other solid supports include hydrogels, including collagen hydrogels that are commonly used in eyedrops and eardrops. These, too, may be linked to suitable ophthalmic and otological agents using the invention methods and compositions. Anti-glaucoma drugs as well as drugs designed to treat macular degeneration, for example, may be thus coupled.

Another commonly employed medical device which is a solid support is a catheter. Typically, catheters, especially those that are designed for long residence times, may be coupled to drugs appropriate for treatment, but also to antibiotics to prevent infection.

Hydrogels may also be used as implants to support stem cell therapies, and release of growth factors for such stem cells through the methods of the invention by linking them to the hydrogel matrix is an aspect of the invention.

The support may also comprise polylactic-glycolic acid (PLGA) polymers. PLGA is a common choice in the production of a variety of biomedical devices, such as grafts, sutures, implants, prosthetic devices, and nanoparticles. Free carboxylate groups can be derivatized.

Also common are implants intended to provide anti-arthritic drugs directly to joints in rheumatoid arthritis patients.

Topical applications include surgical dressings and plasters where the drugs are released externally, and may be designed for treatment of surface wounds or for transdermal entry into the body.

Still other types of solid supports include orthopedic devices which may profitably be coupled to bone growth factors, such as bone morphogenic factor, and dental matrices which may be designed to supply suitable antibiotics and growth factors.

Thus, by "solid support" is meant any material that independently exists as a solid, although the surface may not be smooth or hard, and the solid may be flexible. Thus, hydrogels are included as well as surgical dressings, bandages, physical objects, and the like.

Nature of the Drug Conjugate

The drug conjugate of formula (1) or (2) is designed to control the pharmacokinetics of the drug or prodrug, the residue of which when coupled to the remainder of the molecule is designated as "D". The mechanism whereby the drug or prodrug is released is shown in FIG. 1. The rate of release is controlled according to a pH dependent β-elimination mechanism. The groups $R^1$ and $R^2$ are selected to provide the desired acidity, and thus, reactivity, of the intervening proton in $R^1$—CH—$R^2$, providing control over the rate of drug or prodrug release. The properties of $R^1$ and $R^2$ may be modulated by the optional addition of electron-donating or electron-withdrawing substituents, for example, in aryl moieties contained therein.

In other words, either $R^1$ or $R^2$, or $R^1$ and $R^2$ in combination, can behave as the "trigger" shown in FIG. 1. The nature of the "trigger" controls the acidity of the intervening proton in $R^1$—CH—$R^2$, which, when released, permits the electron pair thus freed to effect β-elimination as shown in FIG. 1 for compounds wherein Y is absent; the first step of the reaction is common to that set forth below when Y is $NBCH_2$.

The mechanism of β-elimination release is thus shown below,

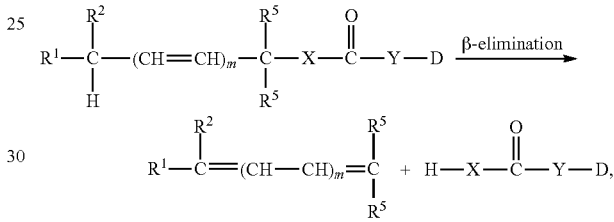

taking place under conditions typical of those of biological systems, for example a pH of between 6 and 8 and a temperature of between 25 and 40° C., at a rate such that the half-life of the reaction is between 1 and 10,000 hours, or between 1 and 5,000 hours, or between 1 and 1,000 hours or between 1 and 100 hours or between 1 and 10 hours. The product acids are typically highly unstable, and further decompose to release $CO_2$ or COS, or $CO_2$, B—$NH_2$, and $H_2C$=O, as well as D-H, depending on the nature of X and Y.

The degree to which the $R^1$ and/or $R^2$ groups activate the adjacent C—H bond may be expressed by the resulting acidity of the C—H bond; this acidity may in turn be expressed as the $pK_a$ of the C—H bond, wherein a lower $pK_a$ denotes a more acidic, more readily ionized C—H bond. Listings of approximate $pK_a$ values for various groups are common in the art, for example in Bordwell, F. G., "Equilibrium acidities in dimethyl sulfoxide solution," *Accounts of Chemical Research* (2002) 21:456-463 (incorporated herein by reference). Examples of suitably activating groups include, but are not limited to, optionally substituted aryls, optionally substituted heteroaryls, optionally substituted alkenes, optionally substituted alkynes, sulfones, sulfoxides, nitriles, ketones, esters, amides, and nitro groups. When the $R^1$ and/or $R^2$ groups are joined to form a 3-8 membered ring, the ring may form part of a larger cyclic structure, optionally substituted, for example

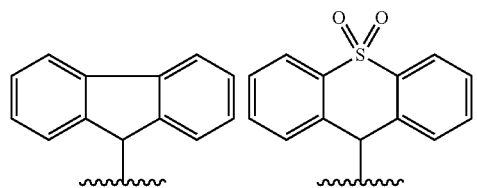

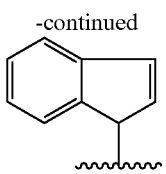

and substituted forms thereof.

Substituents on the $R^1$ and/or $R^2$ groups may optionally be added to provide further control over the acidity of the adjacent C—H, and thus the rate of the beta-elimination reaction. In general, electron-withdrawing substituents will increase the rate of the beta-elimination reaction, while electron-donating substituents will decrease the rate of the beta-elimination reaction. The electronic effect of various substituents is well-known in the art, and may be expressed for example as linear free-energy (Hammett) relationships. For aromatic systems, for example substituted aryl, heteroaryl, arylketone, heteroarylketone, arylsulfone, heteroarylsulfone, arylsulfoxide, and heteroarylsulfoxide groups, the electronic effects of substituents are described by Hammett sigma parameters, with a positive sigma value denoting electron-withdrawing (rate-accelerating relative to an adjacent C—H) and a negative sigma value denoting electron-donating (rate-retarding relative to the C—H) effects. Table 1 provides a listing of Hammett sigma constants for various substituents.

By way of example, where an aryl ring $R^1$ is substituted with an "electron-donating group" is substituent that will result in a decrease in the acidity of the adjacent benzylic-type C—H bond. Examples of suitable electron-donating substituents include but are not limited to, alkyl, alkoxy, alkylthio, silyl amino, alkylamino, and dialkylamino. Substitution of an aryl ring with one or more "electron-withdrawing groups" results in an increase in the acidity of the adjacent benzylic-type proton. Examples of suitable electron-withdrawing substituents include, but are not limited to, halogen, difluoromethyl, trifluoromethyl, nitro, phenyl, alkenyl, cyano, C(=O)—R, wherein R is H, alkyl, alkoxy, or amino, or SOR or $SO_2R$, where R is alkyl, aryl, or heteroaryl. Non-hydrogen electron-donating or electron-withdrawing substituents may be present in multiple positions on rings to which they are bound. While, for convenience, in most examples, only a single occurrence of a non-hydrogen substituent on a single ring is shown, multiple substituents may also be present and are within the scope of the invention. The substituents may be the same or different.

The foregoing is something of an oversimplification, because in some cases, whether a substituent is electron-withdrawing or electron-donating depends on its position in an aromatic ring. This is reflected in the following table of linear free energy (Hammett) relationships, where a positive sigma value denotes electron-withdrawing effect and a negative sigma value indicates an electron-donating effect. As shown in the table, for example, OMe is electron-withdrawing when present in the meta position of a phenyl ring but electron-donating in the para (or ortho) position.

TABLE 1

Selected Hammett sigma constants for aromatic substituents

| Substituent | σ(meta) | σ(para) | Substituent | σ(meta) | σ(para) |
|---|---|---|---|---|---|
| H | 0 | 0 | F | +0.34 | +0.06 |
| $CH_3$ | −0.07 | −0.17 | Cl | +0.37 | +0.23 |
| $CH_3CH_2$ | −0.07 | −0.15 | Br | +0.39 | +0.23 |
| $Me_2CH$ | −0.05 | −0.15 | I | +0.35 | +0.18 |
| $Me_3C$ | −0.1 | −0.2 | SH | +0.25 | +0.15 |
| $Me_3Si$ | −0.04 | −0.07 | MeS | +0.15 | 0 |
| $NH_2$ | −0.16 | −0.66 | $ClCH_2$ | +0.11 | +0.12 |
| $Me_2N$ | −0.15 | −0.83 | $CF_3$ | +0.43 | +0.54 |
| OH | +0.12 | −0.37 | CN | +0.56 | +0.66 |
| OMe | +0.12 | −0.27 | CHO | +0.35 | +0.42 |
| $OCH_2CH_3$ | +0.10 | −0.24 | $CH_3C=O$ | +0.38 | +0.50 |
| AcNH | +0.07 | −0.15 | $CO_2H$ | +0.37 | +0.45 |
| Ph | +0.06 | −0.01 | NO | +0.62 | +0.91 |
| $CH_2=CH$ | +0.05 | −0.02 | $NO_2$ | +0.71 | +0.78 |
| HC(=O)NH | +0.19 | 0 | $Me_3N^+$ | +0.88 | +0.82 |

The remaining substituents $R^5$, m, and B have a lesser effect on the rate of beta-elimination, but the nature of B in particular influences the rate of a competing, largely pH-independent, E1 elimination reaction when Y is $NBCH_2$. The nature of the B group influences the stability of the N-methylene-carbamate toward decomposition via E1 elimination. B groups that reduce the reactivity of the carbamate N lone pair, for example via extended conjugation and/or electron-withdrawing ability, reduce the rate of this competing E1-elimination pathway.

The solid supports may be coupled to formulas (1) or (2) through additional "connectors." The additional connectors are bifunctional organic compounds. Many such connectors are commercially available, for example from Pierce Chemical Co, Rockford, Ill. Various bifunctional connectors are well known in the art, including dicarboxylic acids or anhydrides, diamines, or heterobifunctional connectors. Examples of heterobifunctional connectors include, for example, those having a succinimidyl ester ("NHS") and an alkyne or cycloalkyne (for example, DBCO-NHS), a maleimide and an NHS, or similar molecules. The selection of the connector will, of course, depend on the nature of the functional groups on the substituents on the macromolecule, the drug, and on the intermediates corresponding to Formulas (1)-(4).

The term "alkyl" includes linear, branched, or cyclic saturated hydrocarbon groups of 1-8 carbons, or in some embodiments 1-6 or 1-4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds. By the term "alkenyl ($C_2$)" is meant a mono-, di-, tri-, or tetra-substituted carbon-carbon double bond of any geometric configuration.

The term "alkynyl" includes non-aromatic unsaturated hydrocarbons with carbon-carbon triple bonds. By the term "alkynyl ($C_2$)" is meant a mono- or di-substituted carbon-carbon triple bond.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instances, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4-8 membered aromatic or non-aromatic ring comprising 3-7 carbon atoms and at least one N, O, or S atom. Examples include piperidinyl, piperazinyl, tetrahydropyranyl, pyrrolidine, and tetrahydrofuranyl, as well as the exemplary groups provided for the term "heteroaryl" above.

"Maleimido" refers to formula

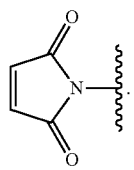

A "nucleofuge" is a leaving group that takes with it the electron pair by which it is bonded. Exemplary nucleofuges are halogen, OH, alkoxy, hydroxysuccinimidyl, arylsulfonate, alkylsulfonate, or $R_2S^+$, wherein each R is independently alkyl, aryl, or heteroaryl.

The terms "protein" and "peptide" are used interchangeably regardless of chain length, and these terms further include pseudopeptides which comprise linkages other than amide linkages, such as $CH_2NH_2$ linkages as well as peptidomimetics.

The terms "nucleic acids" and "oligonucleotides" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins as well as pseudopeptide bonds and bases not found in nature in the case of nucleic acids as well as backbone modifications such as peptide nucleic acids.

The term "small molecule" in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

A wide variety of drugs may be included as the embodiment of D. Each of these drugs will be coupled through a nitrogen, oxygen or sulfur to the remainder of the molecule. Thus, suitable drugs will be those that possess a hydroxy, thiol, or free NH to allow for coupling to the linker. Notably, more than 50% of approved small molecule drugs possess an aliphatic hydroxyl or thiol group or a phenolic hydroxyl group, and more than 40% contain a primary or secondary amine, sulfonamide, amide, imide, or heterocyclic NH (such as a pyrrole or indole). Thus, most approved drugs would be amenable to conjugation according to the invention. In particular, the invention contemplates conjugation of a drug moiety through a primary or secondary hydroxyl, a phenol, a heteroaryl-OH, a thiol, a thiophenol or a heteroaryl-SH; or a "non-basic N". The term "non-basic N" refers to a nitrogen that is part of an NH group in a free drug molecule DH, wherein the NH is characterized by having a pKa less than or equal to about 20. In certain embodiments, the non-basic N is a member of a primary or secondary amide, a primary or secondary sulfonamide, an imide, or a heteroaryl NH (such as that present in pyrrole, pyrimidine, indole, or purine) (collectively, "non-basic NH" groups).

Examples of suitable drugs include those for human or veterinary use including, but not limited to, antidiabetic drugs; growth promoters; antibacterials including aminoglycosides, penicillins, cephalosporins, macrolides and peptides, trimethoprim, piromidic acid, and sulfamethazine; analgesic and anti-inflammatory drugs, antiallergic and anti-asthmatic drugs, antihypercholesterolemic drugs, beta-adrenergic blockers and antihypertensive drugs, antineoplastic drugs, and antiviral drugs.

Further examples of such drugs include alcohols such as paclitaxel and analogues, epothilones and analogues, camptothecin and analogues such as irinotecan, and nucleosides such as 5-fluorouracil and capecitabine. In another embodiment, the drug is a peptide comprising a serine residue. In another embodiment, the drug is a small molecule comprising an arylol group; examples of such drugs include SN-38, etilefrine, prenalterol, and estradiol. In another embodiment, the drug is a peptide comprising a tyrosine residue. If coupling is through S, the drug may be a small molecule comprising a thiol group. Examples of such drugs include penicillamine, captopril, and enalapril. The drug may be a small molecule comprising a thioaryl or thioheteroaryl group; examples of such drugs include 6-mercaptopurine. If coupling is through a non-basic N, the drug may be a small molecule or peptide comprising a primary or secondary amide (such as a pyroglutamate residue or other amide) or sulfonamide, or a heteroaryl group such as an indole (e.g., tryptophan) or purine. Examples include thyrotropin-releasing hormone, bombesin, luteinizing hormone-releasing hormone, follicle-stimulating releasing hormone, octreotide, 5-fluorouracil and allopurinol.

Other drugs are peptide, protein, and nucleic acid drugs. Examples of peptide drugs suitable for use in the invention include, e.g., glucagon-like peptide 1 (GLP-1), atrial natriuretic factor (ANF), and many others. Examples of protein drugs include immunotoxin SS1P, enzymes such as adenosine deaminase, arginase, and others, growth factors, antibodies and cytokines, for example.

Examples of nucleic acid-based drugs include the sense strand and antisense strand of any gene from an animal, and particularly from a mammal. Such genes can be those that are already the subjects of antisense DNAs or RNAs, or small interfering RNAs that have been provided with the purpose of treating various diseases, for example genes for protein kinase C-alpha, BCL-2, ICAM-1, tumor necrosis factor alpha and the like. Additional examples include viral delivery agents for nucleic acids.

The term "precursor" refers to a derivatized solid support similar to that of formula (1) or (2), but wherein rather than linked to the drug or prodrug, the linking compound is coupled to a nucleofuge for further binding to a drug or prodrug as in formula (3)

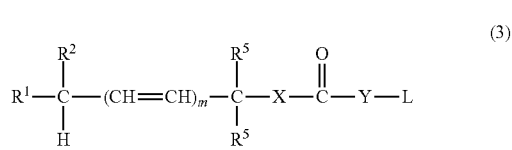

(3)

wherein $R^1$, $R^2$, $R^5$, X, Y and m are as defined as in formula (1) or (2); and wherein L is a nucleofuge.

While typically, the active form of the drug is directly released from the conjugates of the invention, in some cases, it is possible to release the active drug in the form of a prodrug thereof. On example of such a system is shown below:

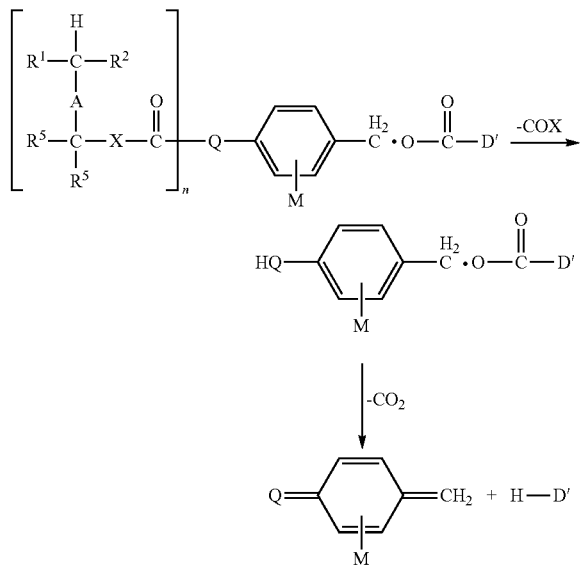

wherein A is $-(C\!=\!C)_m-$, Q=O or NH, D'H is the free drug, and

M is H or is at least one suitable aryl substituent.

To avoid misunderstanding, the "drug conjugates" described herein include conjugates both of drugs and prodrugs.

Exemplary Substituents

Because the groups $R^1$, $R^2$, $R^5$, X, and Y are shared by all of the compounds of formulas (1)-(3) and any intermediates in their preparation, the various embodiments of these groups as presented in the alternative set forth below in connection with the compounds of formula (1) or (2) may be extrapolated to precursors and intermediates thereto. When any group may itself be optionally substituted, the substitution on any ring system may be alkyl, alkyenyl, alkynyl, or an additional ring, each optionally substituted. Optional substituents on any group, including the above, include halo, nitro, cyano, OR, SR, $NR_2$, OCOR, NRCOR, COOR, $CONR_2$, SOR, $SO_2R$, $SONR_2$, $SO_2NR_2$, wherein each R is independently alkyl, alkenyl, alkynyl, aryl or heteroaryl, or two R groups taken together with the atoms to which they are attached form a ring.

Compounds of the invention contain a linkage to a solid support via one of $R^1$, $R^2$, $R^5$, and B (formulas (1), (2), and (3)), or one of $R^1$, $R^2$, $R^5$, and B comprises a functional group that allows for connection to a solid support (formula (4)). Suitable functional groups that allow for connection to a solid support include amino, azido, hydroxy, carboxylic acid, alkynyl, thiol, maleimido, furan, cyclopentadiene, 1,3-diene, or 1,3-dicarbonyl groups, or protected variants thereof. Substituents that comprise a reactive functional group include alkyl, aryl, arylalkyl, heteroaryl, heteroalkyl, or heteroarylalkyl group, substituted with a reactive chemical moiety. Thus, at least one of the $R^1$, $R^2$, $R^5$, and B groups comprises a solid support or comprises one or more amino, azido, hydroxy, carboxylic acid, alkynyl, thiol, maleimido, furan, cyclopentadiene, 1,3-diene, or 1,3-dicarbonyl groups, or protected variants thereof. In some embodiments, $R^1$ is coupled to a solid support or comprises a functional group allowing for connection to a solid support. In some embodiments, $R^5$ is coupled to a solid support or comprises a functional group allowing for connection to a solid support.

As noted above, in the compounds of the invention, $R^1$ and $R^2$ together exert the most control over the release rate for the drug, though $R^5$ and m have some impact as well. In some instances, one of $R^1$ and $R^2$ is hydrogen or is alkyl, arylalkyl or heteroarylalkyl and the other comprises one of the remaining embodiments set forth hereinabove. In other instances, neither of $R^1$ and $R^2$ is hydrogen or is alkyl, arylalkyl or heteroarylalkyl.

For example, $R^1$ may be H and $R^2$ optionally substituted phenyl or both $R^1$ and $R^2$ may be optionally substituted phenyl. The substitutions on the phenyl rings may be at 1-5 positions but preferably 3 or less. If both $R^1$ and $R^2$ are optionally substituted phenyl, they need not be substituted identically, or may be identically substituted. Suitable substituents include alkoxy, halo, nitro, cyano and the like, for example as indicated in Table 1 above.

In other embodiments, one or both of $R^1$ and $R^2$ is $R^6S-$, $R^6S(O)-$, or $R^6S(O)_2-$, wherein $R^6$ is alkyl, substituted alkyl, dialkylamino, alkylarylamino, diarylamino, an N-linked heterocyclic ring, aryl, substituted aryl, heteroaryl, or substituted heteroaryl. The remaining member of $R^1$ and $R^2$ may then be, H, for example, or any of the alternative embodiments set forth above. In particular embodiments, one of $R^1$ and $R^2$ is $R^6S(O)_2-$, wherein $R^6$ is methyl, morpholino, unsubstituted phenyl, or phenyl substituted with one or more halo, methyl, methoxy, or trifluoromethyl groups, and the other of $R^1$ and $R^2$ is H. In further embodiments, one of $R^1$ and $R^2$ is phenylsulfonyl, 4-(trifluoromethyl)phenylsulfonyl, 4-chlorophenylsulfonyl, 4-methylphenylsulfonyl, 4-methoxyphenylsulfonyl, 2,4-dimethylsulfonyl, 2,4,6-trimethylphenylsulfonyl, morpholinosulfonyl, or methanesulfonyl, and the other of $R^1$ and $R^2$ is H.

In other instances, one or both of $R^1$ and $R^2$ may be cyano and the other optionally selected from H or the permissible substituents set forth above, in particular phenyl optionally substituted at one or more positions, for example, with halo, CN, $NO_2$, methoxy and the like.

In another set of instances, one or both of $R^1$ and $R^2$ is optionally substituted benzoyl and the other is hydrogen or any of the other suitable choices, such as optionally substituted phenyl. In further embodiments, one of $R^1$ and $R^2$ is aminocarbonyl, such as N,N-dialkylaminocarbonyl, or morpholinocarbonyl, and the other is H.

In additional embodiments, one of $R^1$ and $R^2$ is any one of the particular embodiments described above, further comprising a connection to the solid support, (or a functional group allowing for connection to the solid support, as in formula (4)) and the other of $R^1$ and $R^2$ is H.

When $R^1$ and $R^2$ are joined to form cyclic structures, this includes groups wherein the $R^1$—CH—$R^2$ moiety forms a substructure such as, for example,

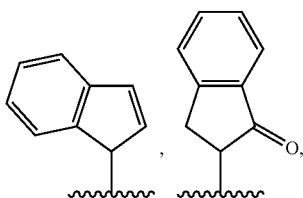

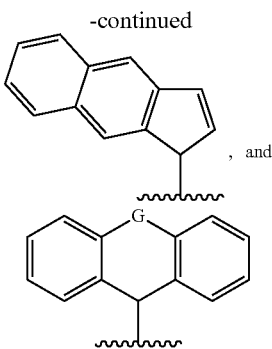

, and

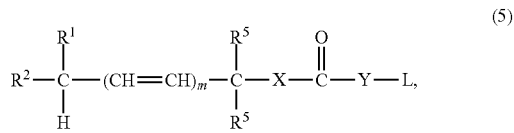

and forms thereof optionally substituted with electron-withdrawing and/or electron-donating groups as described above, wherein G is a bond (e.g., 9-fluorenyl), C=O, SO, $SO_2$, $CG_2$, or $CG_2CG_2$ wherein each G independently is H or Cl. Such cyclic structures may further comprise a connection to the solid support (or a functional group allowing for connection to the solid support, as in formula (4)).

In further embodiments, $R^1$ and $R^2$ taken together with the CH to which they are attached form unsubstituted fluorenyl or fluorenyl further comprising a connection to the solid support. In certain embodiments, $R^1$ and $R^2$ taken together with the CH to which they are attached form fluorenyl or fluorenyl substituted with an alkyl azide, in particular (azido-N-methyl $(CH_2)_{3-6}$alkyl-amido)methyl.

Each $R^5$ is independently H, or is alkyl, alkenylalkyl, alkynylalkyl, aryl, arylalkyl, heteroaryl or heteroarylalkyl, each optionally substituted. In certain embodiments, each $R^5$ is H. In other embodiments, one of $R^5$ is H and the other is substituted alkyl or substituted phenyl. In still other embodiments, one of $R^5$ is H and the other comprises an azidoalkyl group. In still other embodiments, one of $R^5$ is H and the other is azido-$(CH_2)_{3-6}$alkyl, monoalkylamino-$(CH_2)_{3-6}$alkyl, $N_3(CH_2)_{3-6}N(Me)CO(CH_2)_{3-6}$—, or —$(CH_2)_{3-6}$—$CO_2H$, or a protected variant thereof. In additional embodiments, one of $R^5$ is any one of the particular embodiments described above, further comprising a solid support or a functional group allowing for connection to a solid support, and the other $R^5$ is H. In some embodiments, one of $R^5$ is H and the other is phenyl-NHC(O)$R^y$, where $R^y$ is azido-$(CH_2)_5$—, HCC—$(CH_2)_3$—, or (maleimido)-$CH_2CH_2$—.

In preferred embodiments of the invention, B is optionally substituted aryl, or optionally substituted heteroaryl. In one embodiment of the invention, B is aryl or heteroaryl, each substituted with at least one group having a positive Hammett sigma constant (Table 1). In one specific embodiment of the invention, B is phenyl or phenyl substituted with alkoxycarbonyl, carboxamido, sulfonamido, CN, $NO_2$, or Br. In further embodiments, B is unsubstituted phenyl. In still further embodiments, B is unsubstituted phenyl or phenyl substituted with diethylaminocarbonyl, morpholinocarbonyl, or morpholinosulfonyl. In still further embodiments, B is phenyl, propargyl, 4-bromophenyl, 4-ethoxycarbonylphenyl, propyl, 4-(N,N-diethylcarboxamido)phenyl, 4-morpholinocarbonylphenyl, or 4-morpholinosulfonylphenyl. In still further embodiments, B is phenyl, 4-(N,N-diethylcarboxamido)phenyl, 4-morpholinocarbonylphenyl, or 4-morpholinosulfonylphenyl. In additional embodiments, B is any one of the particular embodiments described above, further comprising a solid support or a functional group allowing for connection to a solid support.

In certain embodiments, m is 0.
In other embodiments, X is O. In other embodiments, Y is $NBCH_2$.

In other embodiments, the present invention contemplates compounds of Formula (X):

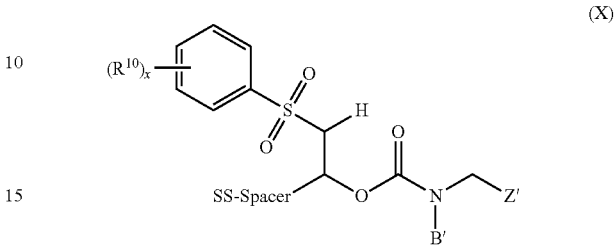

(X)

wherein
x is 0, 1, 2, or 3;
each $R^{10}$ is independently methyl, trifluoromethyl, methoxy, or halo;
B' is phenyl, optionally substituted with alkoxycarbonyl, carboxamido, sulfonamido, CN, $NO_2$, or halo;
Z' is a residue of a drug or prodrug coupled through O, S, or N or is a nucleofuge which permits such coupling;
Spacer is linker comprising an alkyl, heteroalkyl, aryl, or aralkyl group, each optionally substituted; and
SS is a solid support or is a functional group allowing for connection to a solid support.

In other embodiments, the present invention contemplates solid supports of formula (2), wherein m is 0; $R^1$ is phenylsulfonyl, substituted phenylsulfonyl, methanesulfonyl, $(R^9)_2$N—$SO_2$, wherein $R^9$ is defined as for formula (2), or CN; $R^2$ is H; one $R^5$ is optionally substituted alkyl and the other $R^5$ is H; and B is phenyl or substituted phenyl, wherein one of $R^1$, $R^5$, and B further comprises a connection to the solid support.

Synthesis of the Compounds of Formulas 1 or 2

The compounds of formulas (1) or (2) are derived from precursors and intermediates where either the drug/prodrug or the solid support is added as the last step. Thus, in one pathway, a compound of the formula $$R^2 \underset{H}{\overset{R^1}{-C-}} (CH=CH)_m \underset{R^5}{\overset{R^5}{-C-}} X \overset{O}{\underset{\|}{-C-}} Y-L, \quad (5)$$

wherein $R^1$, $R^2$, $R^5$ or B (if present) are not yet coupled to the solid support, can be used as an intermediate. Either the drug/prodrug or the solid support may be coupled first. If the solid support is coupled first, the novel compounds of formula (3) wherein a solid support is coupled to one of $R^1$, $R^2$, $R^5$ or B (if present) are formed. Alternatively, an intermediate containing the drug/prodrug can be first formed and then coupled to the solid support (e.g., formula (4)).

Thus, one step in the synthesis is coupling the remainder of the molecule to the solid support; thus, intermediates are synthesized which contain functional groups in the appropriate $R^1$, $R^2$, $R^5$ or B substituents that permit such coupling.

Methods for conjugation of the intermediates or precursors to solid supports are generally known in the art. In one method, an amide linkage is formed between an amino group and a carboxylic acid group; thus, a precursor or intermediate comprising an amino group can be conjugated to a solid support comprising a carboxylic acid group, or a precursor comprising a carboxylic acid group can be conjugated to a solid support comprising an amino group.

For example, a titanium surface is first modified with a siloxane reagent such as (3-aminopropyl)triethoxysilane (APTES), and the resulting amine-coated surface is reacted with a linker comprising a carboxylate group in the presence of a coupling reagent, for example a carbodiimide, phosphonium, or uranium reagent, to effect a carboxamide bond to the surface. (Xiao, et al., *Langmuir* (1998) 14:5507-5516.)

Alternatively, the surface may first be treated with a heterobifunctional connecter, which is then reacted with a linker comprising a complimentary functional group. In one example, the amine-coated surface is reacted with an alkynoic acid, for example 5-hexynoic acid, under similar conditions so as to produce an alkyne-coated surface. The alkyne-coated surface is then coupled to an azido-linker-drug under Cu(I) catalysis to couple the linker-peptide via a 1,2,3-triazole. Similarly, the amino-coated surface is reacted with a cyclooctyne-containing carboxylic acid so as to produce a cyclooctyne-coated surface, which is coupled to an azido-linker-drug via a 1,2,3-triazole under copper-free conditions.

In another alternative, the amine-coated surface is reacted with an heterobifunctional connecter comprising an N-hydroxysuccinimidyl ester or carbonate on one end and a maleimido group on the other end, for example 4-(maleimido)butyryloxy succinimide. This results in formation of a maleimido-coated surface, which is then coupled to a thiol-linker-drug.

Other reagents for modification of titanium surfaces are known in the art and may be used in the present invention, for example mono-functional aminosilanes (Pegg, et al., *J. Biomed. Materials Res. Part A* (2008) pp. 947-958).

As noted above, with an amine-coated surface conjugation may be performed by reacting the precursor and solid support in the presence of a condensing agent, for example a carbodiimide such as dicyclohexylcarbodiimide (DCC) or 1-(3-dimethylaminopropyl)-3-ethylcarbodiimide (EDCI), a uronium reagent such as O-benzotriazole-N,N,N',N'-tetramethyluronium-hexafluorophosphate (HBTU), or a phosphonium reagent such as benzotriazole-1-yl-oxy-tris-(dimethylamino)phosphonium hexafluorophosphate (BOP).

Alternatively, the carboxylic acid group may be activated for conjugation in a prior step, for example by conversion to an acid chloride using thionyl chloride or oxalyl chloride, or to an active ester such as a pentafluorophenyl ester using a carbodiimide and pentafluorophenol or an N-hydroxysuccinimidyl ester using a carbodiimide and N-hydroxysuccinimide, and the resulting activated carboxylate may then be reacted with the amine in a second step. The amine and carboxylic acid groups may initially be present in protected form as required for stability and/or compatibility with additional chemical transformations, and deprotected prior to the conjugation step. Amine groups may be protected as carbamates, preferably tert-butoxycarbonyl ($^t$BOC), allyloxycarbonyl (Alloc), or other carbamate groups that may be removed under neutral-to-acidic conditions. Carboxylic acids may be protected as esters that may be removed under neutral-to-acidic conditions, such as tert-butyl ($^t$Bu), trityl ($Ph_3C$), allyl (All), or methoxymethyl (MOM).

As further noted above, a thioether linkage is formed between a thiol group and a maleimide group; thus, a precursor comprising thiol group can be conjugated to a solid support comprising a maleimide group, or a precursor comprising a maleimide group can be conjugated to a solid support comprising a thiol group. The thiol group may initially be present in protected form as required for stability and/or compatibility with additional chemical transformations, and deprotected prior to the conjugation step. Suitable protecting groups include those that may be removed under neutral-to-acidic conditions, for example tert-butyl thioethers ($^t$Bu) or trityl thioethers.

Also as noted above, a 1,2,3-triazole linkage is formed between an alkyne and an azide group; thus, a precursor comprising an alkyne group can be conjugated to a solid support comprising an azide group, or a precursor comprising an azide group can be conjugated to a solid support comprising an alkyne group. The conjugation reactions may be performed under metal catalysis, typically using copper or ruthenium, or may be performed in the absence of catalyst using an activated alkyne such as a cyclo-octyne.

In another method, an enamino-ketone linkage is formed between an amino group and a 1,3-dicarbonyl group; thus, a precursor comprising an amino group can be conjugated to a solid support comprising a 1,3-dicarbonyl group, or a precursor comprising a 1,3-dicarbonyl group can be conjugated to a solid support comprising an amine group.

Thus, the $R^1$, $R^2$, $R^5$, or B groups in the intermediate (e.g., formulas (4) and (5)) independently may comprise optionally protected amine, optionally protected carboxylic acid, optionally protected thiol, maleimide, alkyne, or azide groups to allow for conjugation with solid supports. Once conjugated, the $R^1$, $R^2$, $R^5$, or B groups independently may optionally be substituted by solid supports connected via carboxylic amide, thioether, or 1,2,3-triazole groups.

In addition, to increase the loading on a solid surface, the intermediate, with or without drug, may be attached to the surface via a multi-valent carrier, such as a dendrimeric or branched carrier.

Thus, in addition to the linking methods set forth above, such linkages may be through dendrimers or polyvalent macromolecules coupled to the compound of formula (5) or drug conjugates. This is described in application Ser. No. 13/696,301, now U.S. Pat. No. 8,703,907, issued on Apr. 22, 2014, which is hereby incorporated by reference. The intermediate or drug conjugate is therefore coupled through the dendrimer to the solid support.

In one example, a dendrimer is prepared which comprises a group on the dendrimer that may be selectively coupled to a suitable-modified metallic surface. Suitable groups for such selective coupling include groups such as azides, terminal alkynes, cycloalkynes, thiols, and maleimido groups.

For example, a dendrimer may be prepared by solid-phase synthesis starting from a protected cysteine-resin. Successive rounds of coupling with di-Fmoc-lysine generate a dendrimeric structure. A final round of couplings is performed using Fmoc-L-azidonorleucine. The final Fmoc is removed, and the free amine groups are reacted with a polyethylene glycol activated as its N-hydroxysuccinimide (NHS) ester. The resulting PEGylated dendrimer is then coupled to an alkyne-drug conjugate using Cu(I)-catalysis, and the PEG-dendrimer-drug conjugate is cleaved from the resin using trifluoroacetic acid. The resulting complex comprises a free thiol at the core cysteine, which may be coupled to a maleimido-modified surface prepared as described above. Alternatively, the final round of couplings uses di-Fmoc-lysine; removal of the Fmoc groups, coupling of the dendrimer to linker-drug using any of the above-described methods, and cleavage from the synthesis resin provides a non-PEGylated dendrimer which may be coupled to a maleimido-modified surface.

In some embodiments a functional group on the intermediate is attached directly to a compatible functional group on the solid support. In other embodiments, a functional group on the intermediate is reacted with a linking group attached to the solid support, e.g., a functionalized PEG moiety or a peptide moiety that is attached to the solid support and provides a further functional group that can be reacted with a corresponding functional group on the intermediate molecule. Coupling to such macromolecules is described, for example, in application Ser. No. 13/696,299, now U.S. Pat. No. 8,754,190, issued on Jun. 17, 2014, which is hereby incorporated by reference.

For example, hydroxyl groups on a stent or other medical device coated with a hydroxylated polymer, such as poly (ethylene-co-vinyl alcohol) (EVAL), may be activated, e.g., by reaction with carbonyldiimidazole or triphosgene, and then the activated intermediates may be further reacted with an intermediate containing an amine functional group to provide a urethane linkage between the intermediate and the coated device.

Conjugation of the intermediates of the present invention to medical devices coated with other functionalized polymers, such as carboxylated polymers or amino polymers, including, e.g., poly(vinylamine) (PVA), poly(ethyleneimine) (PEI), poly(N-methyl-ethylene imine) (PMEI), and poly(amino-amines) (PAA), may also be envisioned to react with suitably functionalized intermediates.

Alternatively, a stent coated with the hydroxylated polymer may be activated and reacted with a linking moiety, such as a functionalized PEG, to install a different functional group that may be compatible with other intermediates. For example, reaction of the activated hydroxyl groups with an amino-PEG moiety provides a polymer-coated stent conjugated to PEG via a urethane linkage. The free hydroxyl groups of the PEG moiety can be further reacted, e.g., with a propargylic halide, to install a terminal acetylene group that can undergo cross-coupling with an azide on the intermediate molecule. Other functionalized PEGs, containing groups such as carboxylic acids, amines, thiols, alkynes, etc. can be envisioned that will allow coupling to differently functionalized intermediates.

In other embodiments, the intermediate molecules can be conjugated to materials such as surgical gauzes, surgical sutures (monofilaments, twisted yarns or knitting yarns), absorbent pads, bandages, burn dressings and packings for tooth cavities in the form of cotton, paper, woven or nonwoven fabrics, sponges, and the like, which may comprise either natural polymers (e.g., cellulose, viscose rayon, cellulose acetate, carboxymethyl cellulose, methyl cellulose, agarose, dextran, pectin, alginic acid, chitin, polysaccharides, and proteins such as wool, silk, collagen, galatin and casein), which contain functional groups such as free hydroxyl groups, amines or carboxylic acids. A wide variety of synthetic polymers may also be used.

For example, hydroxyl group-containing polymeric materials, such as cotton or cellulose, may be activated by reaction with polymaleic anhydride or a similar agent to produce a polymer impregnated material containing carboxylic acid functional groups that can undergo amide bond formation with an amine-bearing intermediate under appropriate coupling conditions.

Alternatively, the hydroxylated material can be activated with a variety of other reactive materials to install different functional groups. For example, acylation with bromoacetyl bromide gives a bromoacetyl group that can react with amine-, hydroxyl- or thiol-containing intermediates. In other embodiments, the hydroxylated material can be reacted with a polyaldehyde, such as glutaraldehyde or glyoxal, to introduce formyl groups which can undergo reaction with amine-containing intermediates.

In further embodiments, the intermediate molecules can be conjugated to proteinaceous materials such as collagens, which can optionally be in the form of collagen hydrogels, including those commonly used in eyedrops and eardrop. For example, thiolation of collagen can be accomplished under standard conditions. The surface thiol groups can be further reacted with activating agents, such as carbonyldiimidazole, and then reacted with an amine containing intermediate to provide a thiocarbamate-linked collagen drug conjugate. Alternatively, the thiol groups can be alkylated with, e.g., a propargylic halide, to give terminal acetylene groups that can react with azide containing intermediates. Coupling may also be through acylation of amino groups on the collagen.

Coupling of Drug/Prodrug

For conjugates where Y is absent, coupling of the drug is illustrated below. In formula (A),

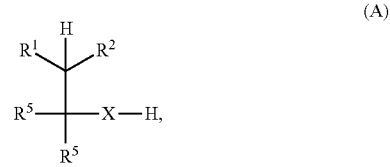

or alkene analogs wherein m is 1 (not pictured), coupling to solid support may or may not have already been conducted. Thus, $R^1$, $R^2$ and $R^5$ are as above-defined or alternatively, one of $R^1$, $R^2$ and $R^5$ is coupled to a solid support. For coupling with a drug or prodrug molecule DH, the alcohol or thiol of formula (A) (or m=1 analogs) is first activated for condensation by reaction with a suitable reagent, for example phosgene or triphosgene, optionally in the presence of N-hydroxysuccinimide; N,N'-disuccinimidyl carbonate; 1,1-carbonyldiimidazole; 1,1-carbonylditriazole; or similar reagents, for the conversion to an activated compound A*, wherein W=F, Cl, imidazolyl, triazolyl, or O-succinimidyl, and then coupled to the drug DH for form a compound of formula (3) (including m=1 analogs thereof).

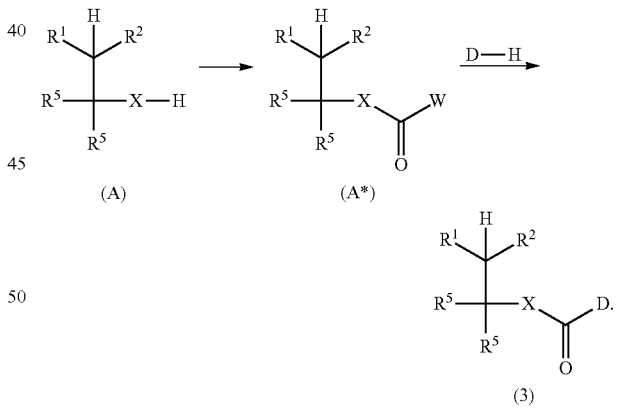

For example, reaction of a compound of formula (A) wherein X=O with triphosgene and N-hydroxysuccinimide yields a compound wherein X=O and W=O-succinimidyl:

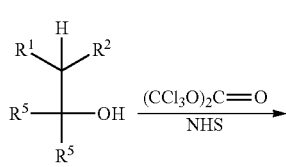

-continued

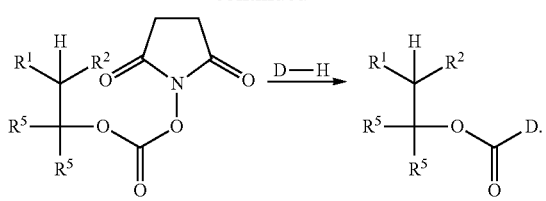 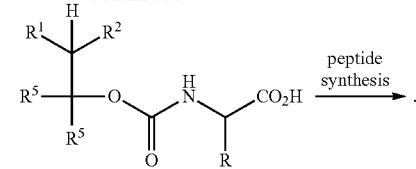

Compounds wherein X=O and W=O-succinimidyl are particularly preferred when the drug or prodrug molecule to be conjugated has an amino group. In this case, the resulting compound comprises a carbamate linkage. For cases wherein the drug or prodrug is a peptide or protein, the amino group that reacts with the intermediate may be a terminal alpha-amino group or the amino group of a side-chain, for example of a lysine, ornithine, or unnatural amino acid residue.

Alternatively, the activating reagent may be a substituted phenyl chloroformate, for example, 4-nitrophenyl chloroformate, 2,4-dinitrophenyl chloroformate, or pentafluorophenyl chloroformate, resulting in formation of an intermediate substituted phenyl carbonate.

Intermediates wherein X=O and W=F or Cl are particularly preferred when the drug or prodrug molecule to be conjugated has no amino group, but instead has a hydroxy group, for example when the drug or prodrug is a peptide or protein from a side-chain tyrosine, serine, or threonine residue, or when the drug or prodrug is nucleic acid-based such as a deoxynucleic acid or ribonucleic acid, or a small molecule.

The precursors wherein the drug is an oligonucleotide or nucleic acid may be prepared by chemical synthesis of the drug comprising a 5'-terminal modification that allows for conjugation. For example, the oligonucleotide may be chemically synthesized such that the 5'-terminal nucleotide unit, added at the last round of synthesis, comprises a phosphate group modified to contain an amino-alkyl group. The resulting amine-modified nucleic acid molecule is then conjugated to form a drug conjugate. See, for example, Zhao, et al., *Bioconjugate Chemistry* (2005) 16(4):758-766.

In the case of peptide-, protein-, or nucleic acid-based drugs, multiple reactive groups may be present leading to multiple reactions. The extent of this multiple reaction may be controlled using standard conditions known in the art, for example by varying the reaction temperature, concentrations, and stoichiometries in order to obtain the desired reaction product.

In one embodiment of the invention, where the drug is a peptide, the intermediate formed by reaction with an amino acid is then employed in standard peptide synthesis, for example:

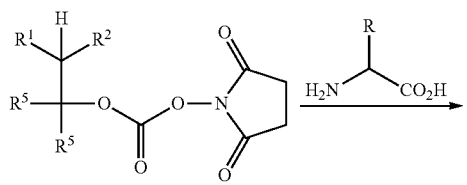

In another method, the intermediate is attached during the synthesis of the peptide. For example, the final step in the synthesis of the peptide by solid-phase peptide synthesis methods well-known in the art involves attachment of the N-terminal amino acid of the sequence of the peptide in protected form. Applying this technology to the present compounds, after deprotection of the final amino acid residue, the activated linker is coupled to the support-bound peptide. Final deblocking and removal from the synthesis resin provides the N-terminally linked peptide:

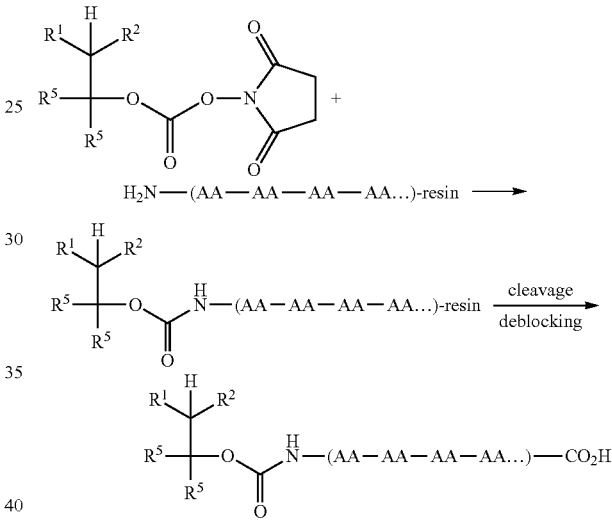

This embodiment is advantageous in that the position and stoichiometry of derivitization is completely controlled.

Preparation of Intermediate Compounds

Compounds of formula (1) are prepared from alcohols $R^1R^2C$—$(C=C)_mC(R^5)_2OH$, in which the solid support is not yet attached to the rest of the molecule. Synthesis of such alcohols is described, for example, in PCT patent application PCT/US2009/048943, published as WO2009/158668A1 (incorporated herein by reference). Examples are given in the working examples provided below.

Alcohols $R^1R^2C$—$(C=C)_mC(R^5)_2OH$ wherein m is 0 (formula (A)) may be prepared by the addition of a carbanion $R^1R^2CH^-$ formed by reacting $R^1R^2CH_2$ with a strong base, for example butyllithium, NaH, lithium diisopropylamide, lithium bis(trimethylsilylamide), or similar, with a molecule to produce a compound of formula (A)

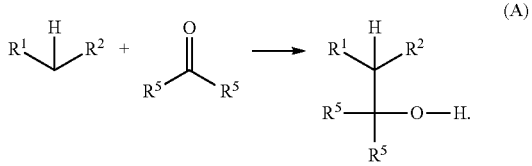

Alternatively, compounds of formula (A) wherein m is 0, X=O and one $R^5$ is H may be prepared by a two-step process. In the first step, the addition of a carbanion $R^1R^2CH^-$ formed by reacting $R^1R^2CH_2$ with a strong base, with an ester $R^5$—C(=O)OR*, wherein R* is lower alkyl, produces an intermediate ketone $R^1R^2CH$—$CR^5$=O, which may in the second step be reacted with a suitable reducing agent, for example $NaBH_4$ or $NaBH_3CN$, to provide the compound of formula (A) wherein X=O, and one $R^5$ is H.

For example, when $R^1R^2CH_2$ is fluorene, this is reacted with a strong base, for example, to form a fluorenyl carbanion, which is then reacted with $R^5_2$—CO, the reaction is as follows:

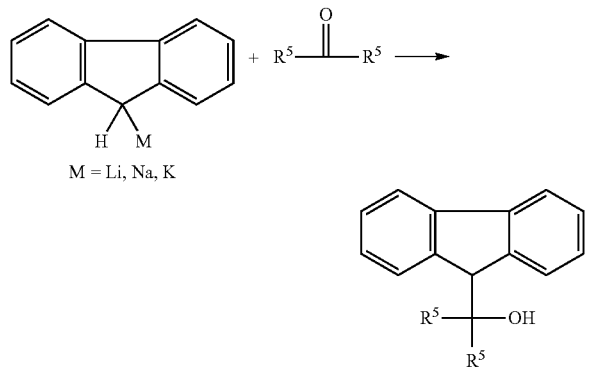

Corresponding compounds wherein X is S may be similarly prepared using the appropriate analogue $R^5_2$—C=S, or may alternatively be prepared by subsequent chemical transformation of formula (A) where X is O using methods known in the art, for example activation of the alcohol group in (A), for example by conversion to a bromide using $PBr_3$ or $Ph_3PBr_2$, or by conversion to the tosylate or triflate, and displacement by a suitable nucleophilic group such as thiourea or thiosulfate. In one embodiment, thiosulfate is used to form an intermediate that is hydrolyzed by acid treatment to form the thiol.

Alcohols $R^1R^2C$—$(C=C)_mC(R^5)_2OH$ wherein m is 1 and both $R^5$ are H may be prepared by addition of the carbanion derived by lithiation of $R^1R^2CH_2$, for example using a strong base such as NaH, butyllithium, lithium bis(trimethyl-silylamide), or similar, to an unsaturated compound such as methyl 3-(dimethylamino)-acrylate to provide an intermediate ester, which may be reduced, either via one step or through multiple steps, to the corresponding unsaturated alcohol:

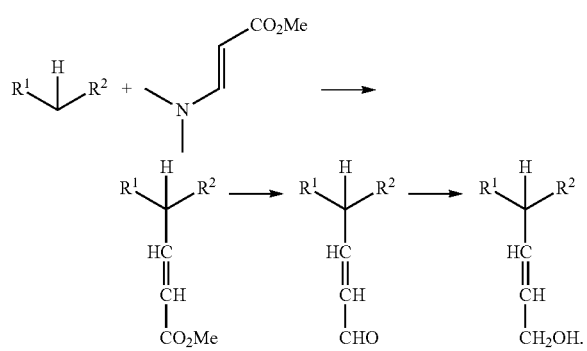

Reaction of the unsaturated aldehyde shown above with a substituted or unsubstituted arylboronic acid, aryl-µ(OH)₂, in the presence of a palladium catalyst, for example as described in *Org. Letts.* (2005) 7:4153-5, provides a compound wherein m is 1, one $R^5$ is substituted aryl, and one $R^5$ is H, and X=O.

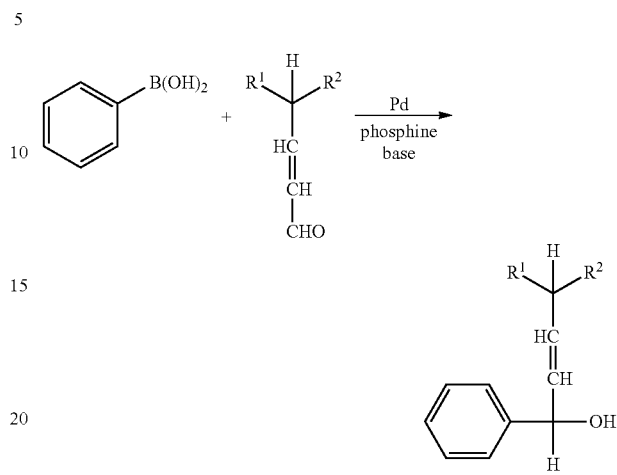

Alternatively, reaction of the unsaturated aldehyde shown above with an alkylborane according to the method of Soderquist provides compounds wherein m is 1, X=O, one $R^5$ is H and the other is —$CH_2CH=CH_2$ or —$CH_2CCH$. See Burgos, C. H., et al., *J. Am. Chem. Soc.* (2005) 127:8044.

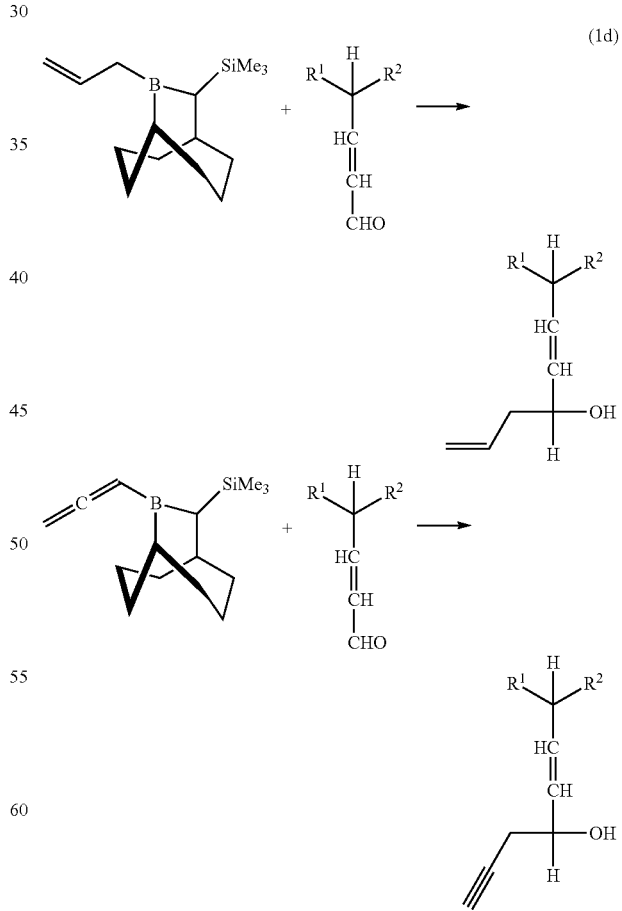

(1d)

The compounds of formula (A), or analogs where m is 1, may then be coupled with the drug. In these intermediates and the drug conjugate, all of the embodiments which correspond to the many illustrated forms of formulas (1) and (2), and specifically embodiments of $R^1$, $R^2$ and $R^5$ are retained.

In instances where Y is $NBCH_2$, an additional intermediate is prepared from the compound of formula (A), or an analog where m is 1, for example, by activating the compound of formula (A) where X is O to a compound of formula (A*), as described above, and then further reacting this compound with a hexahydrotriazine derivative $(BNCH_2)_3$. This results in an intermediate where the leaving group, L, attached to the methylene is a chloro group. Analogs wherein L is another suitable leaving group, such as a tosylate, mesylate, iodide, or $R_2S^+$, are prepared using methods known in the art. Alternatively, alcohols $R^1R^2C—(C≡C)_mC(R^5)_2OH$ are activated as described above, reacted with $B—NH_2$ in the presence of a mild base such as pyridine or $NaHCO_3$ to give a carbamate, $R^1R^2C—(C≡C)_mC(R^5)_2OC(O)NHB$, which is then reacted with paraformaldehyde in the presence of a nucleofuge donor L*. In a specific embodiment, L* is a chloride donor such as $Me_3SiCl$ or HCl, yielding a compound wherein L is Cl. Such intermediates can be reacted with a drug comprising OH, SH or a non-basic NH group under anhydrous conditions in the presence of mild base. Suitable bases include tertiary amines, such as triethylamine and N,N-diisopropylethylamine, pyridine, or 4-(dimethylamino)pyridine. The reaction mixture may optionally include NaI or a tetraalkylammonium iodide to accelerate the reaction. Suitable solvents include any inert, anhydrous solvent, including tetrahydrofuran, acetonitrile, dimethylformamide, ethyl acetate, dichloromethane, acetone, and chloroform.

In some instances, for example when the drug comprises a phenol or non-basic NH, it may be advantageous to pre-form a salt of the drug by reaction with a strong base, for example NaH, lithium bis(trimethylsilylamide), lithium diisopropylamide, or similar.

Attachment of Protective Polymers

The solid supports may also include protective polymer (the most common example would be polyethylene glycol (PEG), but other hydrophilic polymers could also be used). In certain embodiments, the protective polymer is a PEG of average molecular weight between 2,000 and 20,000 Daltons, preferably between 2,000 and 10,000 Daltons, and more preferably between 2,000 and 5,000 Daltons. In certain embodiments, the PEG is a monomethoxy-PEG.

In one approach, only a portion of the reactive sites on the derivatized solid support are provided with drug conjugate or polymer by controlling the stoichiometry of the coupling reaction and the remaining sites are then coupled to the other component.

In another approach, pre-assembled units comprising a PEG, a releasable linker, and a drug, or some combination of these units are prepared, then the pre-assembled units are attached to the solid support. Such pre-assembled units may be constructed in a stepwise process starting from a trifunctional matrix molecule wherein each functionality may be selectively attached to a PEG, the releasable linker or the drug conjugate, and to the solid support. Suitable functionalities on the tri- or multi-functional matrix molecule include carboxylic acids, amines, maleimides, azides, thiols, and alkynes, which may be present in protected form.

For instance, an amino acid comprising a carboxylic acid group and two differentially protected functional groups can be converted into such a pre-assembled unit by selective deprotection of one protected functional group, attachment of a PEG, then deprotection of the second protected functional group and attachment of the drug conjugate, then final attachment of the pre-assembled unit through the carboxylic acid to the solid support. In one example, azidonorleucine is reacted with an activated PEG molecule, for example a PEG N-hydroxysuccinimide carbonate, so as to produce $N_α$-PEG-azidonorleucine. The $N_α$-PEG-azidonorleucine is then either attached to the solid support through standard amide-forming reactions to provide a PEGylated solid support having an array of azide functionalities on the outer shell that can be subsequently coupled with alkynyl-linkers or alkynyl-drug conjugates, or is first reacted with an alkynyl-linker or alkynyl-drug conjugate under Cu(I) catalysis to provide the complete pre-assembled unit, which is then attached to a solid support derivatized with amine groups using standard amide-forming reactions.

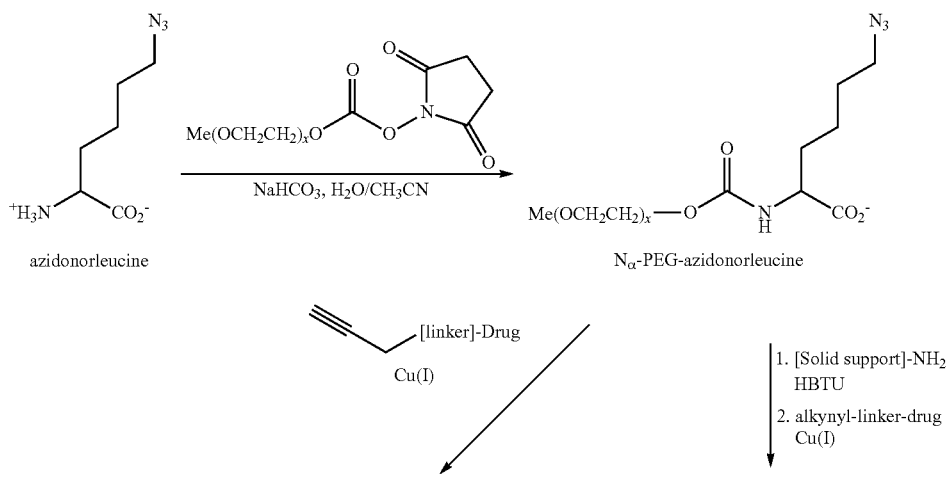

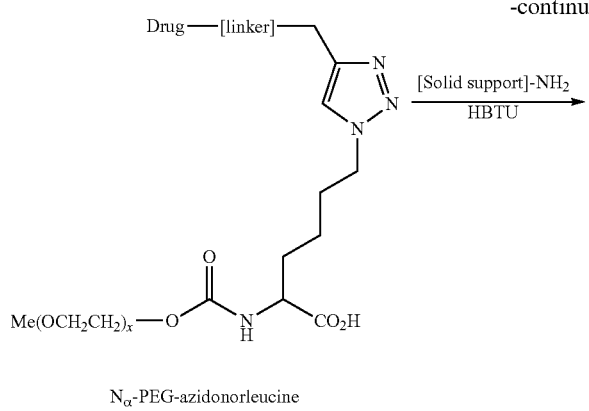
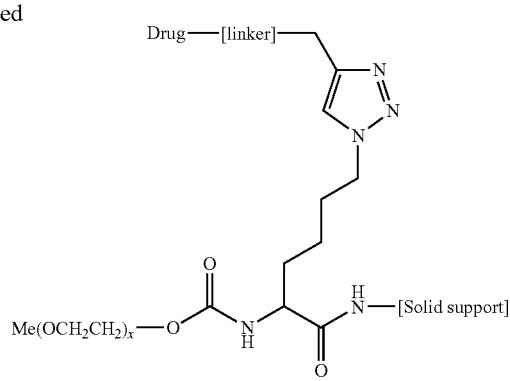

In another example, a protected cysteine, for example S-(monomethoxytrityl)-cysteine, is reacted with an activated PEG molecule, for example a PEG N-hydroxysuccinimide carbonate, so as to produce $N_\alpha$-PEG-S(mmt)-cysteine. This can be attached to a solid support derivatized to amines using standard amide forming reactions, and the resulting solid support can be detritylated using mild acid and the resulting thiols reacted with a maleimide-linker or maleimide-drug conjugate. Alternatively, the $N_\alpha$-PEG-S(mmt)-cysteine can be reacted with an amine-linker or amine drug conjugate using standard amide-forming reactions, and the complete pre-assembled unit can be detritylated using mild acid and coupled to a solid support derivatized to maleimide groups.

human patients or may be veterinary subjects such as companion animals, livestock, and avian subjects. The solid support conjugates may be administered by any of several methods, for example internally as surgical implants, subcutaneous implants, intraocular implants, suppositories, or coated medical devices such as stents, pacemakers, and heart valves, or externally as wound dressings or topical coatings. The dosage levels will depend on the nature of the drug, the condition to be treated, the nature of the subject, and the judgment of the attending professional. The selection of appropriate release rates for a particular drug or protocol are also dependent on these factors. Thus, the use and adminis-

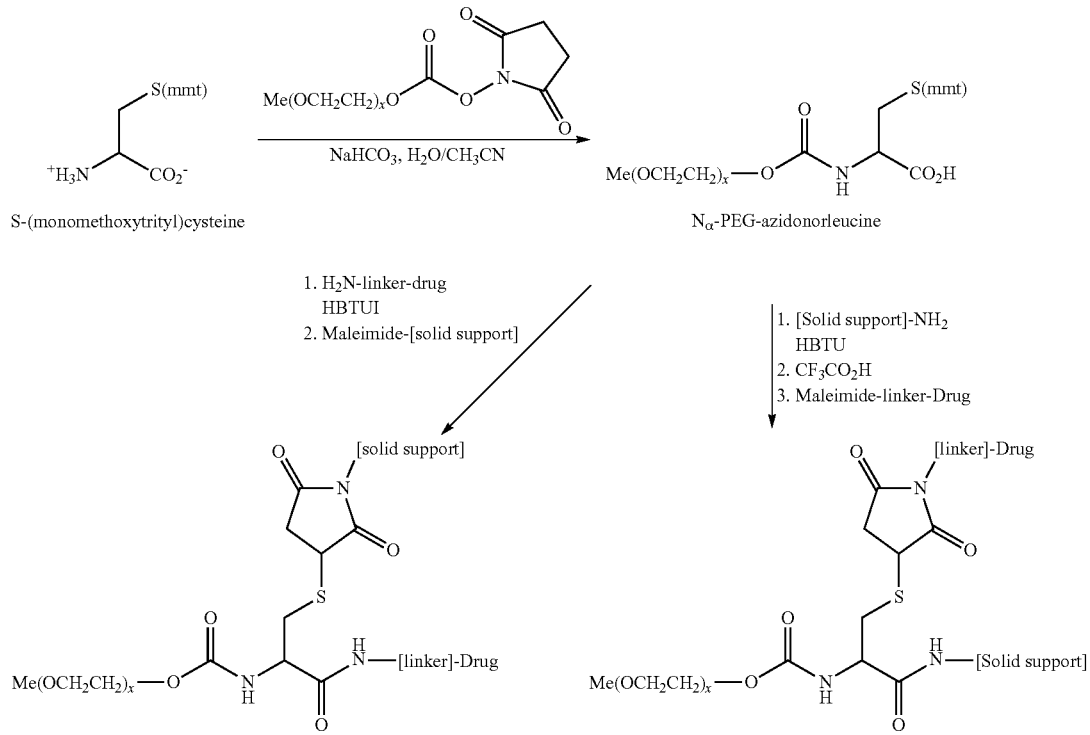

Administration and Use

The conjugates of the invention that are designed to release drugs at controllable rates are administered to subjects in a manner similar to medicaments in general. The subjects may be model systems such as mice, rats or rabbits or may be tration of the compounds of the invention is within the skill of the practitioner. Further, as noted above, the conjugates of the invention are particularly useful and advantageous in treating diseases of the lymph system wherein subcutaneous implantation is preferred.

Unless otherwise stated, all references cited herein are incorporated by reference in their entirety. The following examples are intended to illustrate but not to limit the invention.

Example 1

Release Rate Determination—Phenyl Sulfones

A series of linker scaffolds having a range of functional groups as potential $pK_a$ modulators (substituted aromatics, ketones, nitriles, sulfones) were designed, prepared and linked via carbamate bonds to $N_\epsilon$-2,4-dinitrophenyl-L-lysine ($N_\epsilon$-DNP-Lys) for evaluation of release rates. DNP-Lys was chosen as the released moiety as is water soluble and is a strong chromophore to permit HPLC-UV analysis. This experiment demonstrates that the rate of carbamate cleavage is controllable through the choice of particular substituents on the trigger group.

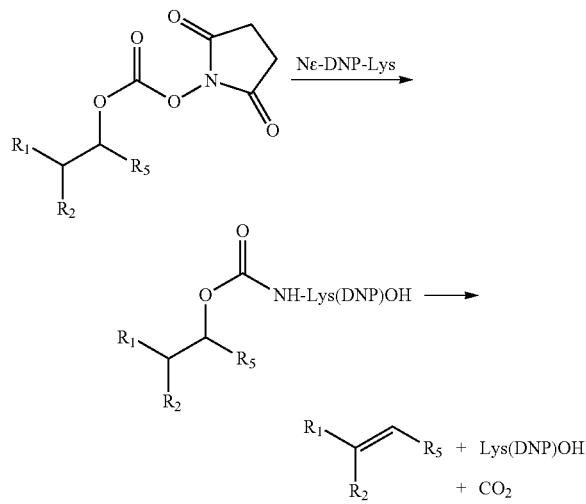

Starting alcohols, obtained commercially or prepared by standard methods, were converted into N-hydroxysuccinimide (HS) carbonates either using a one-step procedure with disuccinimidyl carbonate (Manoharan, *J. Org. Chem.* (1999) 64:6468-6472) or by a two-step procedure wherein the alcohol is first converted into the chloroformate using triphosgene/pyridine and then to the carbonate by treatment with N—HS (Tsubery, H., et al., *J. Biol. Chem.* (2004) 279:38118-38124).

The dinitrophenyl (DNP) carbamates were prepared as follows. A suspension of N-DNP-L-Lys HCl (35 mg, 0.1 mmol) in 600 µL of water was treated successively with 1.0 N NaOH (200 µL) and 1.0 M NaHCO₃. A 0.1 M solution of the N—HS carbonate in acetonitrile (1.0 mL) was added to the stirred mixture to give a clear yellow solution. After 1 hr, the mixture was diluted with 10 mL water and loaded onto a Bond-Elut™ C18 extraction column (1 gm). The column was washed successively with water, 1% $CF_3CO_2H$/water, water, and 50% MeOH/water. The product was eluted with MeOH, then evaporated to give the product as a yellow glass.

The rates of release of $N_\epsilon$-2,4-dinitrophenyl-L-lysine from these compounds were determined at pH 7.4 or pH 8.3, 37° C., by HPLC analysis. Kinetic analyses of the release reactions were performed by HPLC (C18; linear MeOH/water+ 0.5% HOAc gradient) using a UV/vis monitor at 350 nm. The areas under the Lys(DNP) ("P") and starting material ("S") peaks were integrated to determine extent of reaction ("R") as R=P/(S+P). Reaction rates were calculated from the slope the line obtained by linear regression analysis of a plot of ln(1-R) versus time. The $t_{1/2}$ values of β-eliminative cleavage of DNP-Lys carbamates at pH 7.4 and/or 8.3 are shown in Table 2.

TABLE 2

Kinetic data for release of $N_\epsilon$-2,4-dinitrophenyl-L-lysine at 37° C.

| $R^1$ | $R^2$ | $R^5$ | $t_{1/2}$ pH 7.4 | $t_{1/2}$ pH 8.3 |
|---|---|---|---|---|
| 4-MePhSO₂ | H | H, H | 56 hrs | — |
| PhSO₂ | H | H, H | 30 hrs | — |
| 3-NO₂PhSO₂ | H | H, H | 2 hrs | — |
| PhSO₂ | H | H, Me | 72 hrs | — |
| 4-ClPhSO₂ | H | H, Me | 46 hrs | — |
| 4-ClPhSO₂ | H | H, 4-OMePh | 18 hrs | — |
| 4-ClPhSO₂ | H | H, 4-BrPh | 17 hrs | — |
| 4-ClPhSO₂ | H | H, 4-NO₂Ph | 2 hrs | — |
| 4-OMePhSO₂ | H | H, 3-NO₂Ph | 13 hrs | — |
| 4-OMePhSO₂ | H | H, 4-NO₂Ph | 10 hrs | — |
| CN | H | H, H | — | 160 hrs |
| CN | H | H, Me | — | 320 hrs |
| CN | H | H, Ph | — | 98 hrs |
| CN | H | H, 4-BrPh | 270 hrs | — |
| CN | H | H, 4-OMePh | 22 hrs | — |
| CN | 4-OMePh | H, Me | 125 hrs | — |
| CN | 4-NO₂Ph | H, Me | ~80 hrs | — |
| 9-fluorenyl | | H, H | ~1650 hrs | 200 hrs |
| 9-fluorenyl | | H, Me | — | ~1800 hrs |
| 9-fluorenyl | | H, 4-BrPh | — | 285 hrs |

As shown in Table 2, the half-lives for elimination of the carbamate and release of $N_\epsilon$-2,4-dinitrophenyl-L-lysine varied from 2 to >1650 hours at pH 7.4. That cleavage was generated by β-elimination reactions was evidenced by the different half-lives, and the observation that O-benzyl-N—($N_\epsilon$-2,4-dinitrophenyl-L-lysine)-carbamate (which cannot undergo O-alkyl scission) showed no observable release of $N_\epsilon$-2,4-dinitrophenyl-L-lysine (less than the estimated detection limit of 0.25% cleavage) after 5 days at 37° C. and pH 7.4 ($t_{1/2}$>3 yrs).

O-Benzyl-N—($N_\epsilon$-2,4-DNP-Lys) carbamate undergoes no detectable hydrolysis in 50% human serum after 1 week at 37° C. This demonstrates the stability of carbamates to serum hydrolases. In general, compared to C—H, a) electron withdrawing groups at $R^1$ increase the rate; b) alkyl groups at $R^5$ increase the rate; and c) aryl moieties at $R^5$ decrease the rate.

Figure 2:
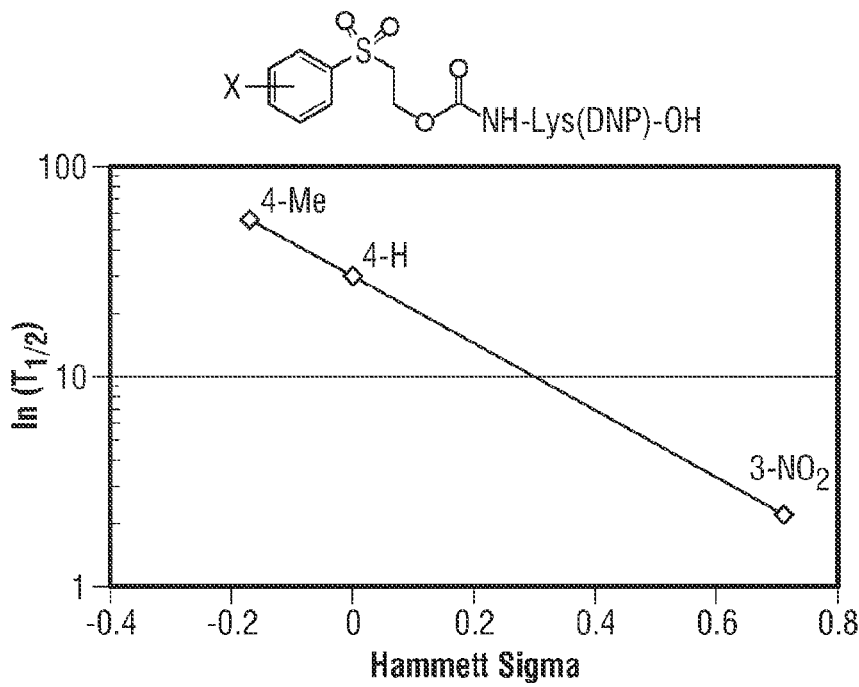
FIG. 2 is a graph showing the relationship of free energy to half-life for release of label from substituted β-elimination compounds through study of a model system, as described in Example 1.

A good linear free energy relationship, shown in FIG. 2, was observed for the substituted (phenylsulfonyl)ethyl linkers, allowing estimation of release rates for other substituted linkers in this series based on SAR using Hammett sigma parameters. Thus, substituents can be selected to provide either slower (e.g., 4-OMe, $\sigma_p$=−0.27; 4-OH, $\sigma_p$=−0.37; 4-Me₂N, $\sigma_p$=−0.83) or intermediate release rates (e.g., 4-F, $\sigma_p$=+0.06; 4-Cl, $\sigma_p$=+0.23; 3-Br, $\sigma_m$=+0.39; 4-CF₃, $\sigma_p$=+0.54).

Example 2

Release Rate Determination—Effect of $R^5$

From the studies in Example 1, the phenyl sulfone moieties at $R^1$ appeared to provide rates ($t_{1/2}$~2 to 72 hr) spanning a range suitable for use in drug conjugates. These were converted into bifunctional linkers containing a N-hydroxysuccinimide (NHS) carbonate for attachment to amine-containing molecules and an acylated 3-aminophenyl moiety at $R^5$ for attachment to solid supports directly or via PEG or dendrimers. In particular, conjugates having the general structure shown below were prepared.

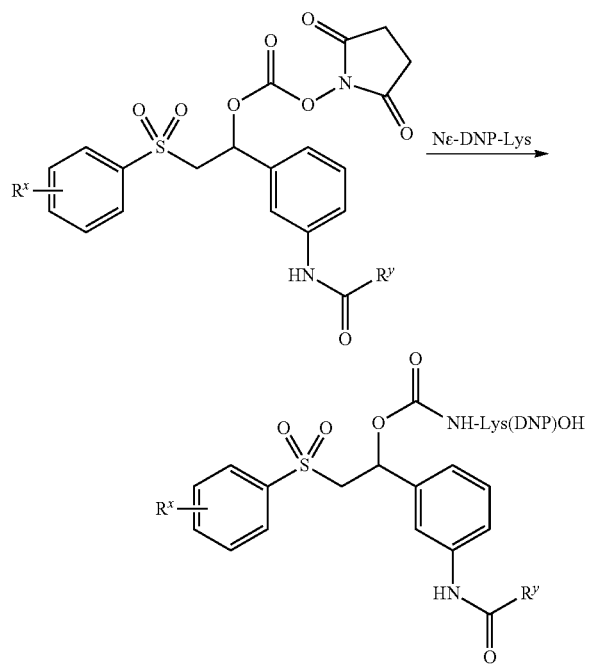

$R^x$=4-chloro, H, 4-methyl, 4-methoxy, 2,4-dimethyl, and 2,4,6-trimethyl;

$R^y$=—$(CH_2)_3C\equiv CH$, —$(CH_2)_5N_3$, —$(CH_2)_2$-maleimide

The NHS carbonate linkers with $R^y$=—$(CH_2)_3C\equiv CH$ were attached to $N_\varepsilon$-DNP-Lys, and the rates of Lys(DNP) release were measured in 0.1 M HEPES, pH 7.40 at 25° C. or 37° C. using HPLC. All compounds gave good first-order kinetics, with $t_{1/2}$ ranging from 16 to 120 hours (Table 3) and a temperature coefficient $Q_{12}$ of 5.7±0.1.

TABLE 3

Rates of H-Lys(DNP)-OH release from compounds
($R^y$ = —$(CH_2)_3C\equiv CH$)

| | | k, hr$^{-1}$ | | $t_{1/2}$, hr | |
|---|---|---|---|---|---|
| No. | $R^1$ | 25° C. | 37° C. | 25° C. | 37° C. |
| 1 | 4-Cl | 0.0074 | 0.0434 | 94 | 16 |
| 2 | H | 0.004 | 0.0236 | 170 | 30 |
| 3 | 2,4-Me$_2$ | 0.0021 | 0.012* | 330 | 57 |
| 4 | 4-Me | 0.0018 | 0.0104* | 380 | 67 |
| 5 | 4-OMe | 0.0013 | 0.0074 | 530 | 94 |
| 6 | 2,4,6-Me$_3$ | 0.001 | 0.0057 | 690 | 120 |

*extrapolated from data at 25° C.

Figure 3:
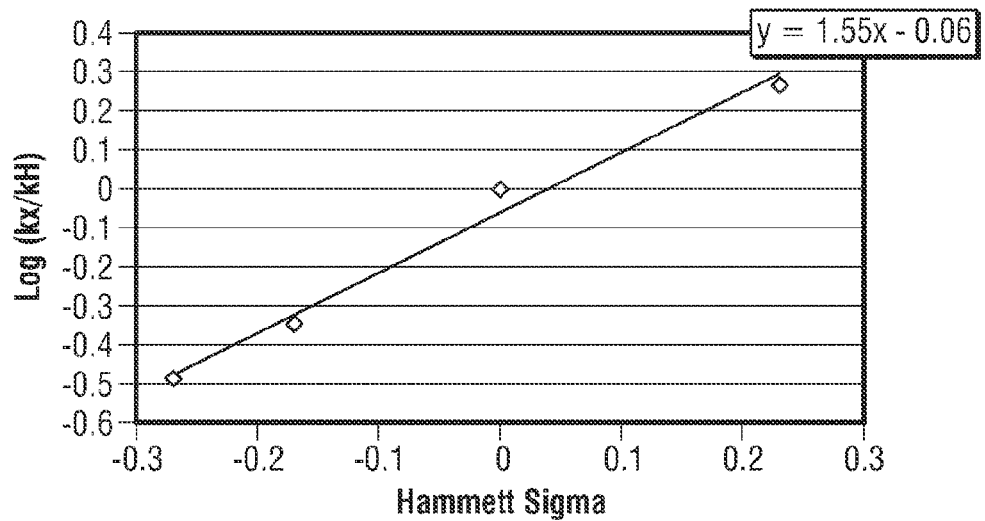
FIG. 3 is a graph showing the free energy correlation between Hammett sigma values and rate of release of label by β-elimination as described in Example 2.

A good correlation between release rate and Hammett sigma constants was also observed for the mono-substituted compounds is shown in FIG. 3.

Example 3

Effect of Coupling to a Macromolecule

The linker with $R^x$=4-methoxy, $R^y$=—$(CH_2)_3C\equiv CH$ coupled to $N_\varepsilon$-DNP-Lys was conjugated with 40 kDa PEG-azide using copper-catalyzed Huisgen cycloaddition. Examination of the release of H-Lys(DNP)-OH indicated that the rate of release from the macromolecular conjugate (k=0.0059 h$^{-1}$, $t_{1/2}$=118 hrs) was similar to that of the unconjugated linker ($t_{1/2}$=94 hr).

Preliminary results of determination of effects of human sera on the rate of release from PEG-conjugates suggest there may be a uniform 3-fold rate enhancement of cleavage. The conjugate of 40 kDa PEG with this compound was administered to rats to determine pharmacokinetics; stably conjugated Lys(DNP) was also prepared by click chemistry between $N\alpha$-hexynoyl-Lys(DNP)-OH and 40 kDa-PEG-azide and administered to rats as a control. Competitive ELISA for DNP-Lys using DNP-BSA and an anti-DNP antibody conjugated to alkaline phosphatase is employed.

Example 4

General Preparation of Chloroformates and N-Hydroxysuccinimide Carbonates

Pyridine (0.33 equivalent) is added dropwise to a vigorously stirred solution of the alcohol $R^1R^2C$—$(C\equiv C)_mC(R^5)_2$OH (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mix is then filtered and concentrated under vacuum on a rotary evaporator. The resulting crude chloroformate $R^1R^2C$—$(C\equiv C)_mC(R^5)_2OC(O)Cl$ is used without further purification.

To prepare N-hydroxysuccinimide carbonates, the crude chloroformate is dissolved in anhydrous tetrahydrofuran (2 mL/mmol) and treated with pyridine (2 equivalents) and N-hydroxysuccinimide (4 equivalents) at ambient temperature for 30 minutes. The mixture is diluted with ethyl acetate, washed successively with 0.1 N HCl, water, and brine, then dried over MgSO$_4$, filtered, and evaporated. The crude carbonates $R^1R^2C$—$(C\equiv C)_mC(R^5)_2OC(O)Su$ are purified by silica gel chromatography (ethyl acetate/hexanes).

Example 5

General Preparation of Carbamates

A solution of the chloroformate of Example 4 (1 equivalent) in acetone (2 mL/mmol) is added dropwise to a vigorously stirred mixture of BNH$_2$ (1 equivalent) and NaHCO$_3$ (2 equivalents) in water (2 mL/mmol). After 30 minutes, carbamates which precipitate as solids are collected by vacuum filtration, washed with water, and dried; carbamates which separate as oils are extracted with ethyl acetate. The extract is dried over MgSO$_4$, filtered, and evaporated to provide the crude carbamate. In either case, the crude carbamate $R^1R^2C$—$(C\equiv C)_mC(R^5)_2OC(O)NHB$ is further purified by column chromatography (SiO$_2$) or by crystallization.

Alternatively, triethylamine (1 equivalent) is added to a mixture of BNH$_2$ (1 equivalent) and the chloroformate (1 equivalent) in an inert anhydrous solvent, for example dichloromethane, tetrahydrofuran, or ethyl acetate. After stirring for 1 h at ambient temperature, the mixture is evaporated to dryness, and the residue is dissolved in ethyl acetate and washed successively with 1 N HCl, water, sat. aq. NaHCO3, and brine, then dried over MgSO4, filtered, and evaporated to provide the crude carbamate, which is purified as described above.

Alternatively, an alcohol $R^1R^2C$—$(C\equiv C)_mC(R^5)_2OH$ is converted to a carbamate without isolation of the intermediate chloroformate. Pyridine (0.33 equivalent) is added dropwise to a vigorously stirred solution of the alcohol (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mixture is cooled on ice, and BNH₂ (2 equivalents) is added. The mixture is allowed to warm to ambient temperature and kept overnight. The mixture is then evaporated to dryness, and the residue is dissolved in ethyl acetate and washed successively with 1 N HCl, water, sat. aq. NaHCO₃, and brine, then dried over MgSO₄, filtered, and evaporated to provide the crude carbamate, which is purified as described above. A drug containing an amine NH moiety may be coupled to the linker directly using the same procedure.

Example 6

N-Chloromethylation of Carbamates

A mixture of the carbamate of Example 5 (1 equivalent) and paraformaldehyde (3 equivalents of formaldehyde) in 1:1 tetrahydrofuran/chlorotrimethylsilane (1 mL/mmol) in a sealed screw-cap vial is heated at 55° C. until a clear solution is obtained. The mixture is concentrated under vacuum on a rotary evaporator, and the residue is dissolved in ethyl acetate, filtered, and concentrated again to provide the crude N-chloromethyl carbamate, $R^1R^2C$—$(C=C)_mC(R^5)_2OC(O)$NBCH₂Cl.

Example 6A

N-Methoxymethyl Carbamates

A solution of N-chloromethyl carbamate of Example 6 in methanol is allowed to stand at ambient temperature for 1 h, then concentrated to dryness to provide the N-methoxymethyl carbamate, $R^1R^2C$—$(C=C)_mC(R^5)_2OC(O)$NBCH₂OMe.

Example 7

N-Alkoxymethyl Carbamates, N-Phenoxymethyl Carbamates, N-Thiomethyl Carbamates, and N-Thiophenylmethyl Carbamates A solution of an alcohol, phenol, thiol, or thiophenol derived from drug DH (1 equivalent) and the N-chloromethylcarbamate of Example 6 (1 equivalent) in an inert anhydrous solvent, for example tetrahydrofuran, dichloromethane, or ethyl acetate, is treated dropwise with triethylamine (1 equivalent). After 1 hour, the mixture is evaporated to dryness. The crude product is purified by silica gel chromatography.

Example 8

O-(9-Fluorenylmethyl)-N-Propargyl Carbamate

A solution of 9-fluorenylmethoxycarbonyl chloride (2.6 g) in 20 mL of acetone was added slowly to a stirred mixture of propargylamine hydrochloride (0.91 g) and NaHCO₃ (2.5 g) in 20 mL of water. After 1 hour, the solid precipitate was collected by vacuum filtration, washed with water, and air dried. Crystallization from ethyl acetate/hexane provided the product.

Example 9

O-(9-Fluorenylmethyl) N-(4-Bromophenyl) Carbamate

Triethylamine (0.7 mL) was added to a stirred mixture of 4-bromoaniline (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO₃, and brine. The organic solution was dried over MgSO₄, filtered, and evaporated.

Example 10

O-(9-Fluorenylmethyl) N-(4-(Ethoxycarbonyl)Phenyl) Carbamate

Triethylamine (0.7 mL) was added to a stirred mixture of ethyl 4-aminobenzoate (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO₃, and brine. The organic solution was dried over MgSO₄, filtered, and evaporated.

Example 11

Conjugation of Hydroxy-Containing Moeity to Linker

This example demonstrates that hydroxy-containing molecules are readily conjugated to the linker moiety.

A.
N-(6-(2,4-Dinitrophenylamino)Hexanoyl-L-Serine Allyl Ester

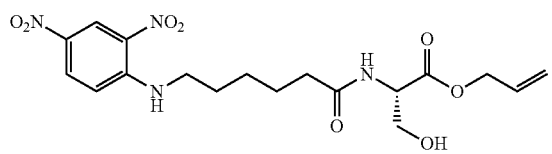 [SMILES: C=CCOC(=O)[C@H](CO)NC(=O)CCCCCNc1ccc([N+](=O)[O-])cc1[N+](=O)[O-]]

Step 1. N-(tert-butoxycarbonyl)-L-serine allyl ester: To a stirred solution of allyl bromide (2.3 mL, 26.6 mmol) and tricaprymethylammonium chloride (4.00 g, 9.90 mmol) in CH₂Cl₂ (35 mL) was added a solution of N-(tert-butoxycarbonyl)-L-serine (1.03 g, 5.02 mmol) and NaHCO₃ (0.43 g, 5.12 mmol) in water (16 mL). The biphasic reaction mixture was vigorously stirred at room temperature for 48 hours. It was diluted with water (50 mL) and extracted with CH₂Cl₂ (3×50 mL). The combined organic extracts were dried over MgSO₄, filtered, and concentrated under reduced pressure to yield a colorless oil (5.95 g). Purification using a Thomson Instruments Single Step 80 g silica gel cartridge eluting with 60% hexanes/40% ethyl acetate produced LR2-1 (1.01 g, 82%) as a colorless oil. ¹H NMR (DMSO-d6) δ 1.37 (9H, s), 3.63 (2H, m), 4.00 (2H, m), 4.53 (2H, m), 4.89 (1H, t, J=6.2 Hz), 5.18 (1H, dd, J=1.4 Hz, J=10.6 Hz), 5.30 (1H, dd, J=1.6 Hz, J=17.1 Hz), 5.84 (1H, m), 6.98 (1H, d, J=8.2 Hz).

Step 2. A solution of N-(tert-butoxycarbonyl)-L-serine allyl ester (0.175 g, 0.731 mmol) in 4 M hydrogen chloride/dioxane (2 mL) was stirred at ambient temperature for 40 minutes. The reaction mixture was concentrated on a rotary evaporator and the crude HCl salt was taken up in anhydrous tetrahydrofuran (3 mL). To this solution was added N-succinimidyl 6-(2,4-dinitroanilino)hexanoate (0.288 g, 0.791 mmol) and triethylamine (102 mL, 0.731 mmol). The reaction mixture was stirred at room temperature for 30 minutes and the solvent was evaporated. The residue was partitioned between ethyl acetate and water and the phases were separated. The organic phase was washed with saturated NaHCO₃ and saturated NaCl. It was dried over MgSO₄, filtered, and concentrated under reduced pressure to yield the crude product (0.293 g) as a yellow oil. Purification using a Thomson Instruments Single Step 12 g silica gel cartridge eluting with 50% hexanes/50% ethyl acetate followed by ethyl acetate gave the product (0.222 g, 72%) as a yellow oil. $^1$H NMR (DMSO-d6) δ 1.32 (2H, m), 1.52-1.64 (4H, m), 2.15 (2H, t, J=7.0 Hz), 3.44 (2H, m), 3.59 (1H, m), 3.66 (1H, m), 4.33 (1H, m), 4.55 (2H, m), 5.02 (1H, t, J=5.5 Hz), 5.17 (1H, m), 5.28 (1H, m), 5.83 (1H, m), 7.21 (1H, d, J=9.5 Hz), 8.12 (1H, d, J=7.9 Hz), 8.23 (1H, dd, J=2.5 Hz, J=9.4 Hz), 8.85 (2H, m).

B. O—(N-((9-Fluorenylmethoxy)Carbonyl)-N-Phenyl)Aminomethyl) N-(6-(2,4-Dinitrophenylamino) Hexanoyl)-Serine

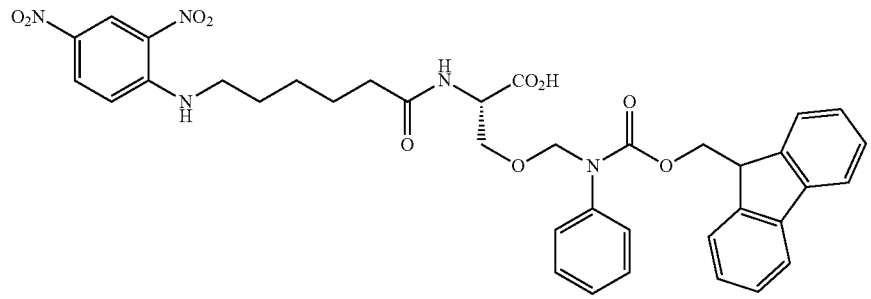 [SMILES: O=C(CCCCCNc1ccc([N+](=O)[O-])cc1[N+](=O)[O-])N[C@@H](COCN(C(=O)OCC1c2ccccc2-c2ccccc21)c1ccccc1)C(=O)O]

Step 1. A solution of N-(6-(2,4-dinitrophenylamino)hexanoyl-L-serine allyl ester (0.050 g, 0.118 mmol), O-(9-fluorenylmethyl) N-phenyl N-chloromethyl carbamate (0.043 g, 0.118 mmol) and triethylamine (16.1 mL, 0.116 mmol) in anhydrous CH$_2$Cl$_2$ (2 mL) was heated at reflux for 1 hour. Further aliquots of O-(9-fluorenylmethyl) N-phenyl N-chloromethyl carbamate (0.043 g, 0.118 mmol) and triethylamine (16.1 mL, 0.116 mmol) were added and reflux maintained for 1 hour. The solution was cooled to room temperature, diluted with CH$_2$Cl$_2$, washed with saturated NaCl solution, dried over MgSO$_4$, filtered, and concentrated under reduced pressure. The crude material (0.145 g) was purified using a Thomson Instruments Single Step 12 g silica gel cartridge eluting with 50% hexanes/50% ethyl acetate followed by 30% hexanes/70% ethyl acetate to furnish the intermediate allyl ester (0.030 g, 33%) as a yellow oil. $^1$H NMR (DMSO-d6) δ 1.31 (2H, m), 1.52-1.63 (4H, m), 2.15 (2H, t, J=7.3 Hz), 3.41 (2H, m), 3.43-3.70 (2H, br. m), 4.15 (1H, br, m), 4.43-4.54 (5H, br. m), 4.87 (2H, br. m), 5.14 (1H, m), 5.25 (1H, m), 5.79 (1H, m), 7.12-7.38 (12H, m), 7.82 (2H, d, J=7.4 Hz), 8.21 (1H, dd, J=2.5 Hz), J=9.5 Hz), 8.25 (1H, d, J=8.0 Hz), 8.84 (2H, m).

Step 2. Tetrakis(triphenylphoshine)palladium(0) (0.002 g, 1.7 µmol) was added to a stirred solution of the allyl ester from Step 1 (0.030 g, 40 µmol) and phenylsilane (9.8 mL, 80 µmol) in anhydrous tetrahydrofuran (0.5 mL). The reaction mixture was stirred at ambient temperature for 30 minutes and was then concentrated. Silica gel and CH$_2$Cl$_2$ were added and the mixture again concentrated and loaded onto a short silica gel column. The column was eluted with 30% hexanes/70% ethyl acetate followed by ethyl acetate and finally ethyl acetate containing 0.5% acetic acid to generate the carboxylic acid (0.024 g, 86%) as a yellow oil. $^1$H NMR (DMSO-d6) δ 1.31 (2H, m), 1.51-1.62 (4H, m), 2.14 (2H, t, J=7.3 Hz), 3.40 (2H, m), 3.45-3.80 (2H, br. m), 4.14 (1H, br. m), 4.41 (3H, br. m), 4.87 (2H, br. m), 7.16-7.30 (12H, m), 7.82 (2H, d, J=7.6 Hz), 8.08 (1H, d, J=8.1 Hz), 8.20 (1H, dd, J=2.7 Hz, J=9.6 Hz), 8.83 (2H, m).

Example 12

O-(9-(2-(N-(6-Azidohexanoyl) N-Methyl)Aminomethyl)Fluorenyl)Methyl) N-Phenyl N-Chloromethyl Carbamate

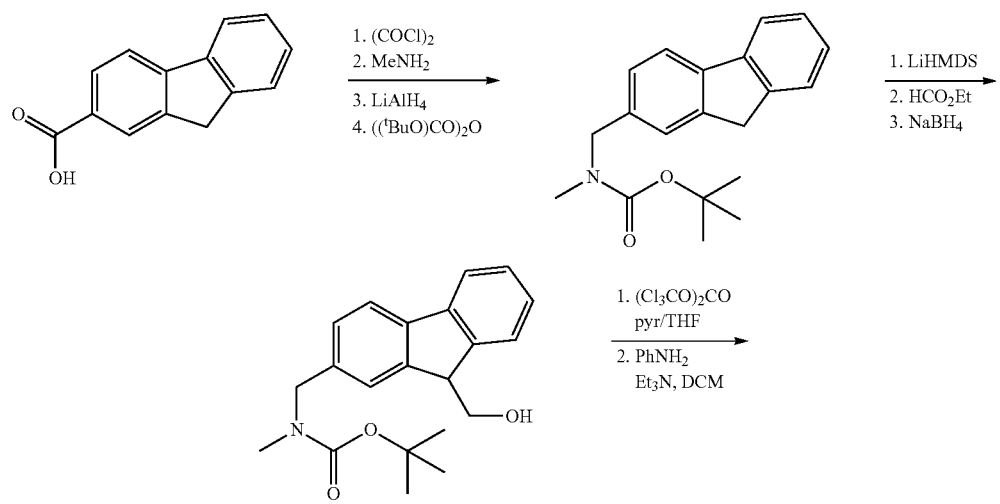

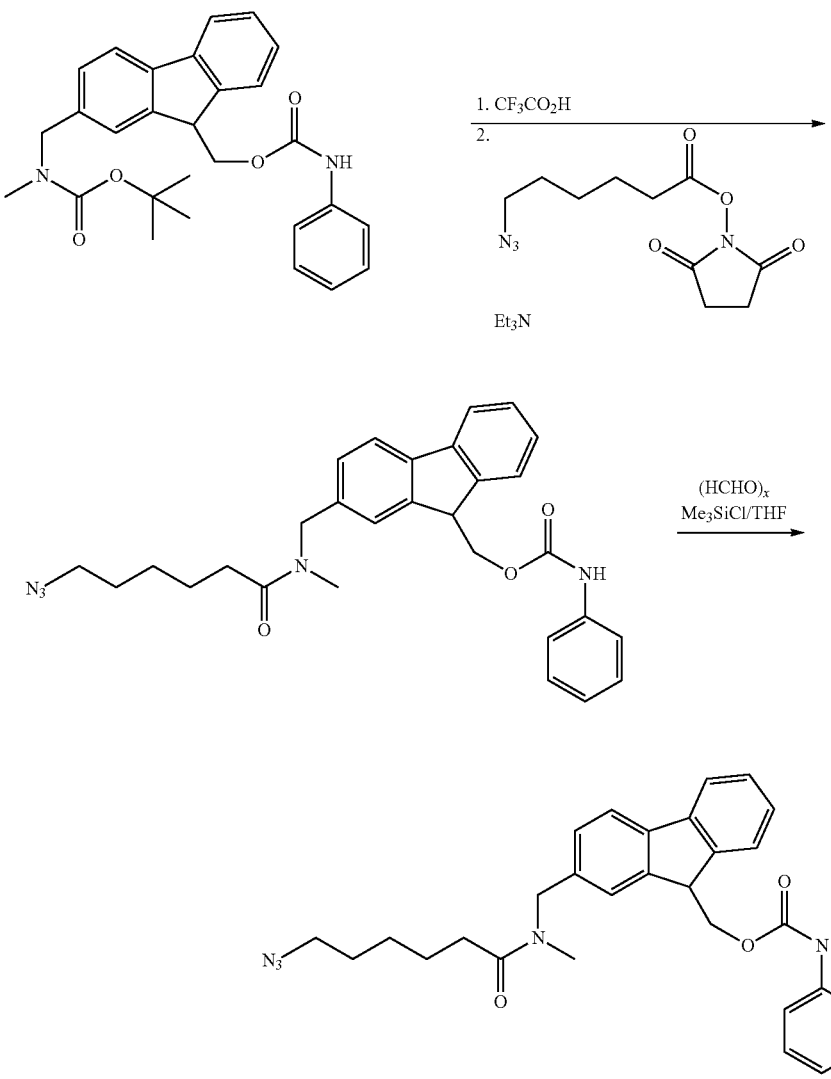

A solution of fluorene-2-carbonyl chloride (prepared from fluorene-2-carboxylic acid and oxalyl chloride) in THF is added to aqueous methylamine (2 molar equivalents) to prepare N-methyl fluorene-2-carboxamide. Reduction of the amide using $LiAlH_4$ in ether provides 2-((methylamino)methyl)fluorene. The amine is protected by reaction with di-tert-butyl dicarbonate to provide 2-((N-$^t$BOC-N-methylamino)methyl)fluorene.

A solution of the 2-((N-$^t$BOC-N-methylamino)methyl) fluorene in anhydrous tetrahydrofuran (THF) is cooled to −78° C., then treated with a solution of lithium bis(trimethylsilyl)amide in THF (1.2 molar equivalents). After 1 hr, ethyl formate is added and the mixture is allowed to warm to ambient temperature. The mixture is diluted with ethyl acetate and washed successively with 0.1 N HCl, water, saturated aqueous $NaHCO_3$, and brine, then dried over $MgSO_4$, filtered, and evaporated to provide the 2-(((N-$^t$BOC-N-methylamino)methyl)-fluorene-9-carboxaldehyde. This compound is dissolved in methanol and treated with $NaBH_4$ to provide 9-(2-((N-$^t$BOC-N-methylamino)methyl)fluorenyl-methanol.

The 9-(2-((N-$^t$BOC-N-methylamino)methyl)fluorenyl-methanol is dissolved in THF and treated with triphosgene and pyridine according to the general procedure of Example 4 to provide the chloroformate. The chloroformate is reacted with aniline according to the method of Preparation 5 to provide O-(9-(2-((N-$^t$BOC-N-methylamino)methyl)fluorenylmethyl) N-phenylcarbamate.

The carbamate is dissolved in trifluoroacetic acid to remove the $^t$BOC protecting group. After evaporation to dryness, the resulting amine is dissolved in THF and treated with N-(6-azidohexanoyl)succinimide and triethylamine (2 equivalents) to provide O-(9-(2-((N-(6-azidohexanoyl)-N-methylamino)methyl)fluorenylmethyl) N-phenylcarbamate.

Reaction of O-(9-(2-((N-(6-azidohexanoyl)-N-methylamino)methyl)fluorenylmethyl) N-phenylcarbamate with paraformaldehyde in 1:1 THF/chlorotrimethylsilane provides the product N-chloromethyl carbamate.

Example 13

Linker-Drug Compound with SN-38

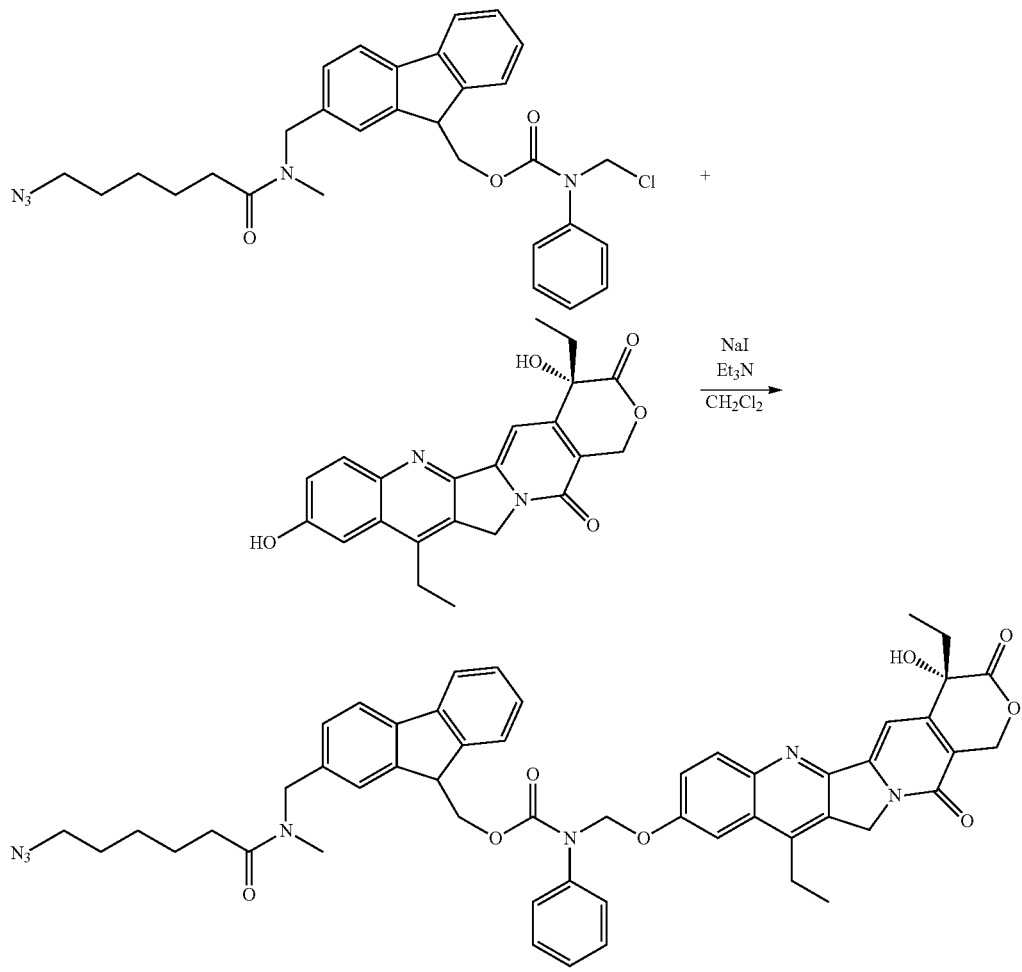

This example demonstrates the linkage of a drug molecule with the compounds of the invention, particularly through a phenol group in the drug molecule.

A solution of the N-chloromethylcarbamate of Example 12 (1 equivalent), SN-38 (1 equivalent), and sodium iodide (10 equivalents) in anhydrous acetone is treated with triethylamine (1 equivalent). The product is purified by silica gel chromatography.

Example 14

General Scheme for Preparation of $R^5$ Azidoalkyl-Linkers

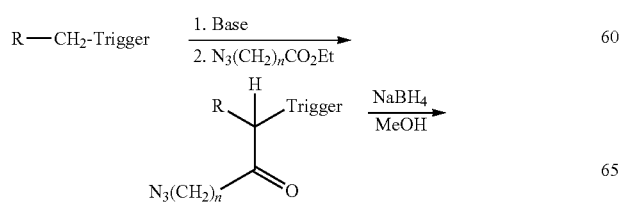

-continued

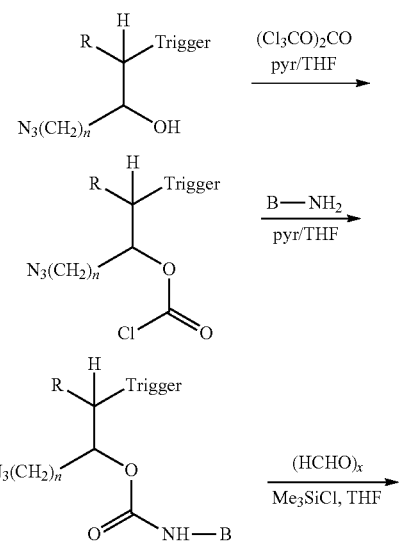

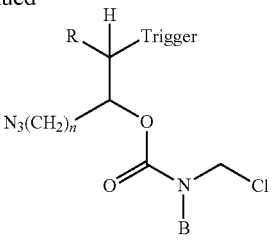

Claisen condensation of R—CH$_2$-Trigger with an ω-azidoalkanoate ester N$_3$(CH$_2$)$_n$CO$_2$R' (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate via the chloroformate, and then into the N-chloromethylcarbamate as described above.

Example 15

General Scheme for Preparation of R$^5$ BOC-Protected Amine Linkers

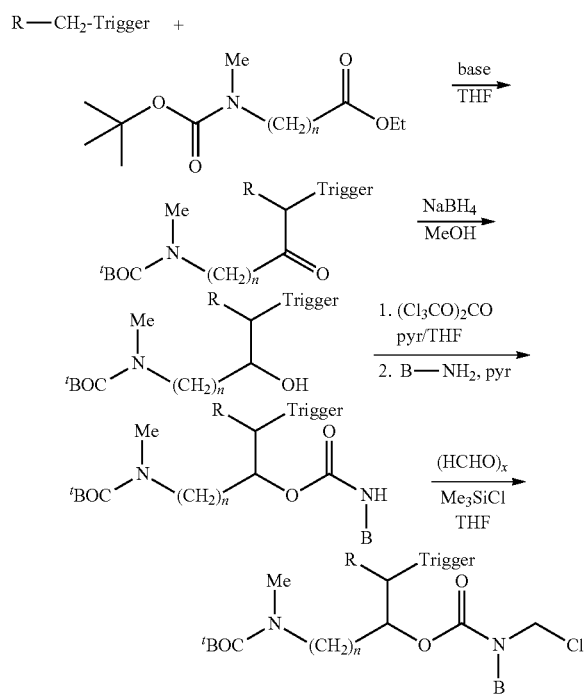

Claisen condensation of R—CH$_2$-Trigger with an ((N-tert-butoxycarbonyl N-alkyl)amino)alkanoate ester (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate using amine B—NH$_2$ as described in Example 5. The carbamate is converted into the N-chloromethylcarbamate as described in Example 6.

After coupling with a drug molecule comprising an alcohol, thiol, phenol, or thiophenol group, the BOC group is removed from the carbamate by treatment with trifluoroacetic acid. The resulting amine is coupled with a macromolecule comprising a carboxylic acid using a condensing agent, for example a carbodiimide such as EDCI.

Example 16

Alternate Scheme for Preparation of R$^5$ Amido-Azidoalkyl-Linkers

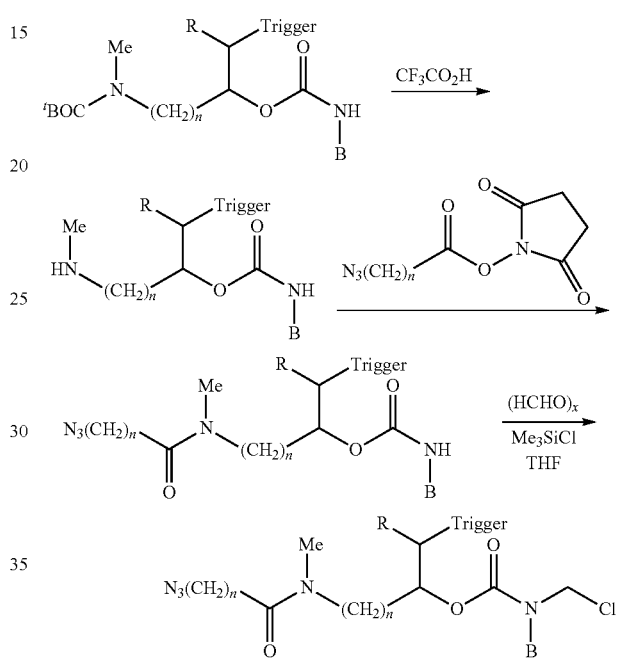

The BOC group is removed from the intermediate BOC-protected carbamate of Example 15 by treatment with trifluoroacetic acid, and reaction of the resulting amine with an azidoalkanoate N-hydroxysuccinimide ester (n=3-6) provides the azidoamide. This is converted into the N-chloromethylcarbamate as described in Example 6.

Example 17

Preparation of a Sulfonyl-Triggered R$^5$ Amine Linker

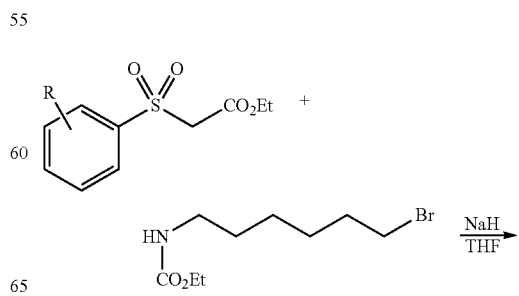

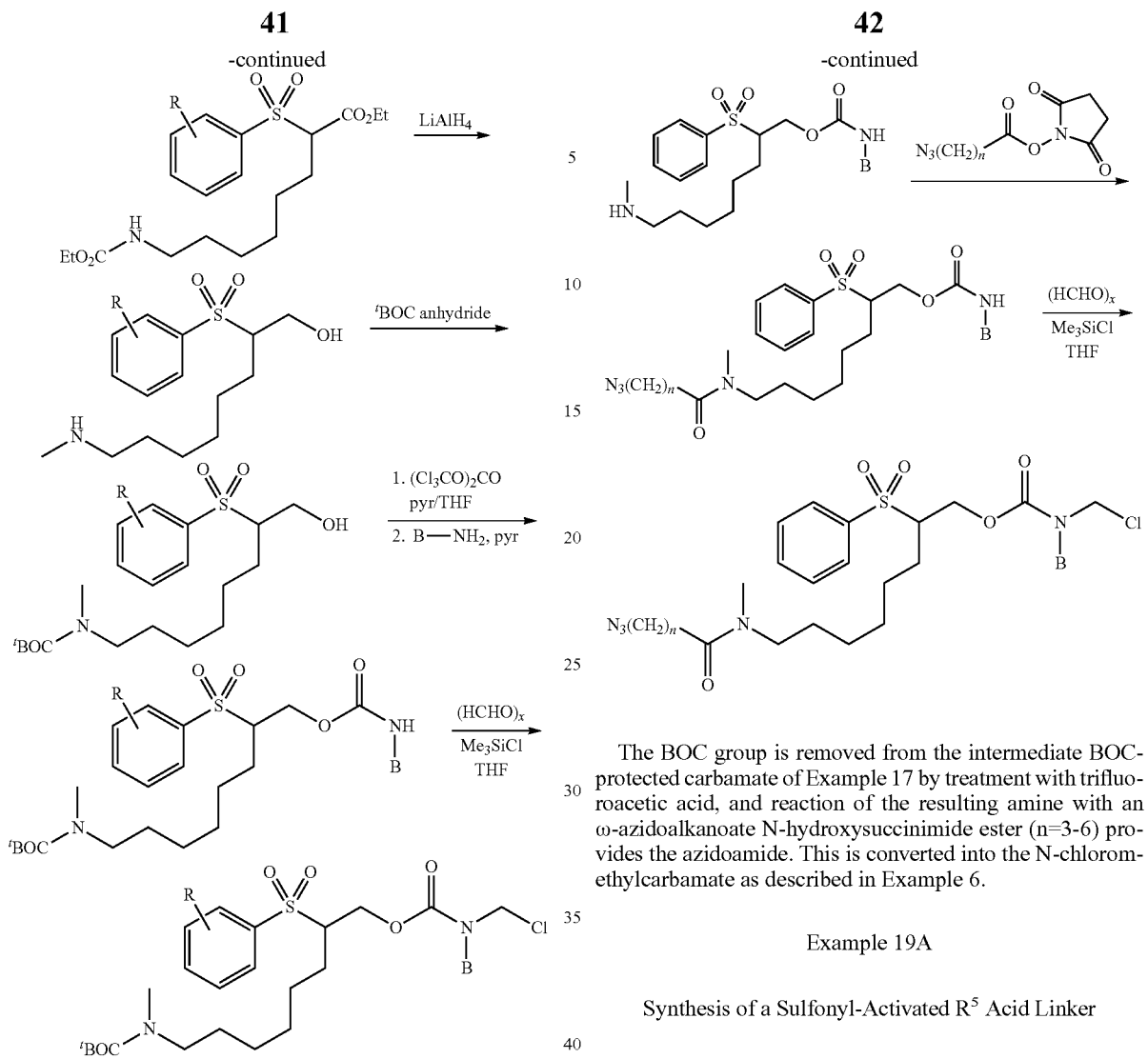

An ethyl (2-phenylsulfonyl)acetate is deprotonated using excess NaH in THF and alkylated with N-(6-bromohexyl) ethyl carbamate. The product is reduced using lithium aluminum hydride in ether to provide the methylamino alcohol, which is N-protected as the BOC carbamate. The alcohol is converted to the chloroformate and thence into the carbamate and into the N-chloromethyl carbamate according to the previous procedures.

Example 18

Preparation of a Sulfonyl-Triggered $R^5$ Amido-Azide Linker

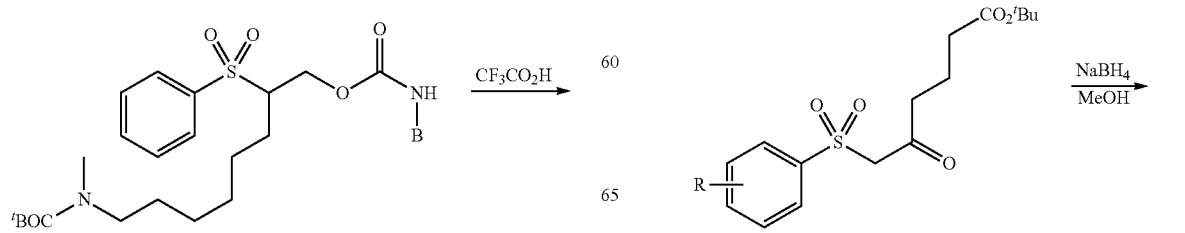

The BOC group is removed from the intermediate BOC-protected carbamate of Example 17 by treatment with trifluoroacetic acid, and reaction of the resulting amine with an ω-azidoalkanoate N-hydroxysuccinimide ester (n=3-6) provides the azidoamide. This is converted into the N-chloromethylcarbamate as described in Example 6.

Example 19A

Synthesis of a Sulfonyl-Activated $R^5$ Acid Linker

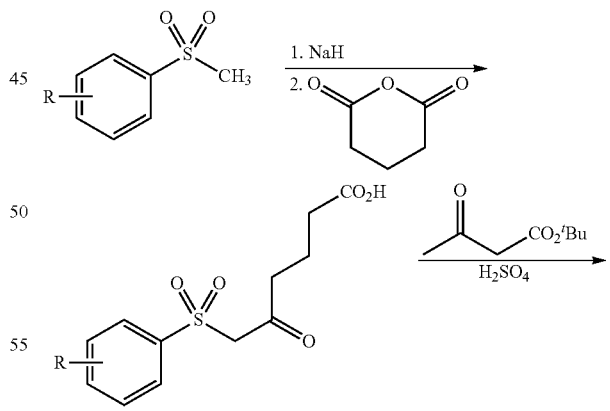

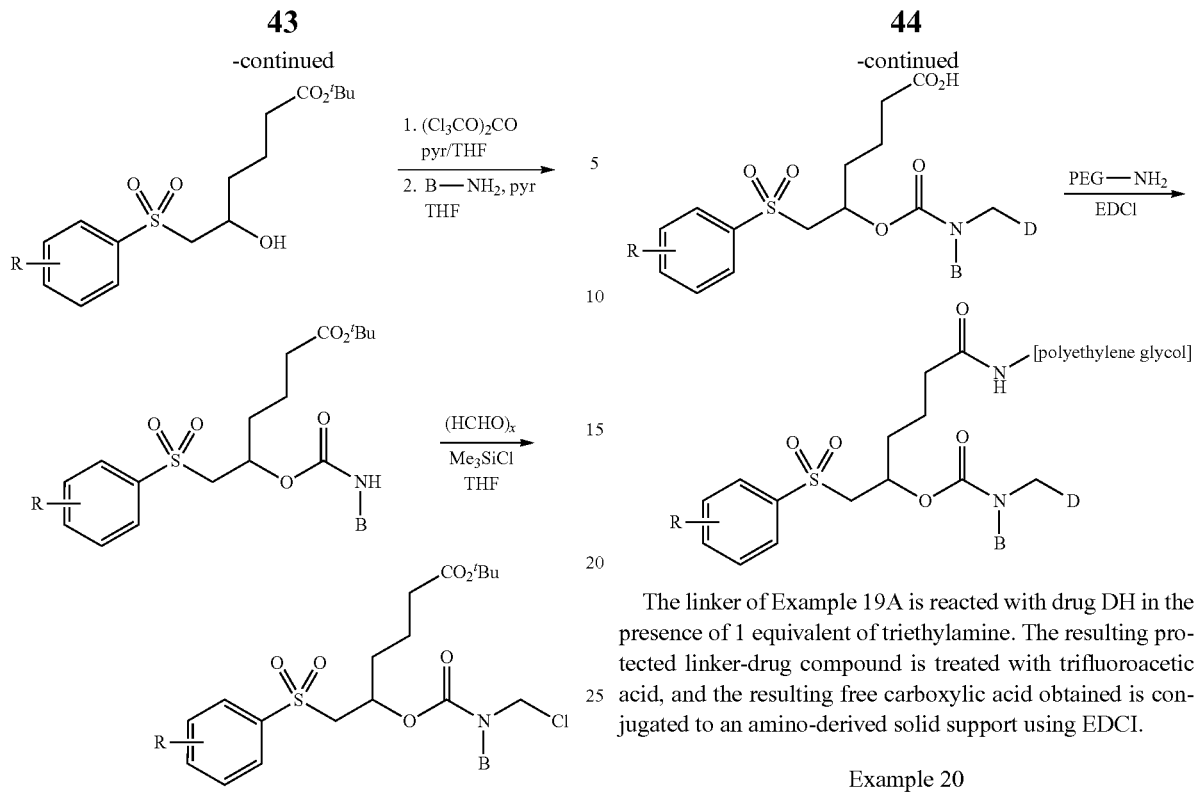

A phenyl methylsulfone is deprotonated with NaH in tetrahydrofuran, then acylated with glutaric anhydride to provide a keto-acid. The resulting acid is protected as the tert-butyl ester, and the ketone is reduced using $NaBH_4$. The resulting alcohol is converted into the carbamate via the chloroformate, and thence to the N-chloromethyl carbamate as described above.

Example 19B

Preparation of a Linker-Drug Compound with a Sulfonyl-Activated Acid Linker and Conjugation to a Solid Support

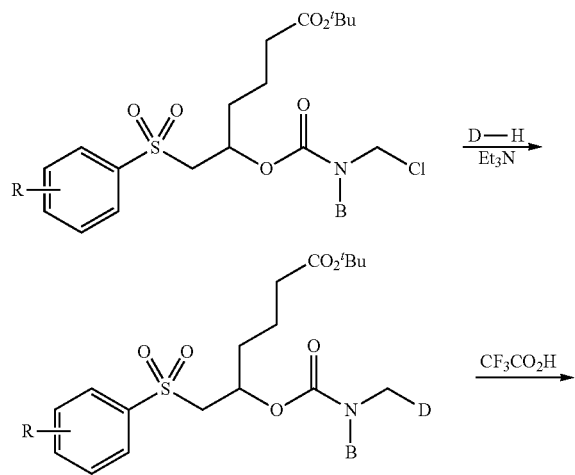

The linker of Example 19A is reacted with drug DH in the presence of 1 equivalent of triethylamine. The resulting protected linker-drug compound is treated with trifluoroacetic acid, and the resulting free carboxylic acid obtained is conjugated to an amino-derived solid support using EDCI.

Example 20

Synthesis of Linked Peptides

This example demonstrates that peptide synthesis is readily accomplished using compounds of the invention. Peptide synthesis is performed using standard methods for solid-phase peptide synthesis, using a serine, tyrosine, or cysteine in a suitably protected form such that the side chains of these residues may be selectively deblocked without deprotection of other residues. The partially deprotected peptide is reacted with an excess of a compound of formula (3) in the presence of a mild base. After washing the resin, the product peptide is deblocked and cleaved from the resin to provide a compound of formula (1) wherein D is a peptide. Alternatively, the solid support may be attached after the peptide is connected to the linker.

As one example, CCK8 (Asp-Tyr-Met-Gly-Trp-Met-Asp-Phe-$NH_2$) is synthesized on solid support using Rink resin using methods known in the art, for example as described in U.S. Pat. No. 4,769,445 (incorporated herein by reference). Commercial Fmoc-Phe-Rink amide-MBHA resin is pre-swollen in DMF for 30 min, then suspended and shaken in piperidine/DMF (1:4 by volume, 50 ml) for 30 min at room temperature to remove the Fmoc group. The product is isolated by filtration and washed (3×50 ml each) with DCM, 5% N,N-diisopropylethylamine (DIEA) in DCM, and DCM to give the free base of Phe-Rink amide-MBHA-Resin. Fmoc-Asp($O^tBu$)-OH (1.23 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Phe-Rink amide-MBHA resin (1 meq) is suspended in the filtered reaction mixture (precipitated DCU removed) and shaken for 2 to 15 hours at room temperature. The Fmoc-Asp-($O^tBu$)-Phe-Rink amide-MBHA resin product is collected by filtration and washed with DCM. The Fmoc-Asp-($O^tBu$)-Phe-Rink amide-MBHA resin is suspended and shaken in piperidine/DMF (1:4 by volume, 50 ml) for 3 min at room temperature and then a second time for 7 min to remove the Fmoc group. The product is isolated by filtration and washed (3×50 ml each) with DMF and DCM to give the free base of Asp-(O'Bu)-Phe-Rink amide-MBHA resin. Fmoc-Met-OH (1.12 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Asp-(O'Bu)-Phe-Rink amide-MBHA resin (1 meq) is suspended in the filtered reaction mixture (precipitated DCU removed) and shaken for 2 to 15 hours at room temperature. The Fmoc-Met-Asp-(O'Bu)-Phe-Rink amide-MBHA resin product is collected by filtration and washed with DCM and DMF. The Fmoc-Met-Asp-(O'Bu)-Phe-Rink amide-MBHA resin is deprotected and coupled sequentially with Fmoc-Trp-OH (1.28 g, 3 mmol), Fmoc-Gly-OH (0.89 g, 3 µmol), Fmoc-Met-OH (1.12 g, 3 mmol), Fmoc-Tyr-OH (1.37 g, 3 mmol), and Boc-Asp (O'Bu)-OH (1.23 g, 3 mmol) to provide Boc-Asp(O'Bu)-Tyr-Met-Gly-Trp-Met-Asp(OtBu)-Phe-Rink amide-MBHA resin. The Boc-Asp(O'Bu)-Tyr-Met-Gly-Trp-Met-Asp (O'Bu)-Phe-Rink amide-MBHA resin is washed with DCM (3×50 ml), suspended and shaken in a mixture of O-(9-fluorenylmethyl) N-phenyl N-chloromethylcarbamate (10 equivalents) and triethylamine (1 equivalent) in DCM. The resin is isolated by filtration and washed (3×50 ml each) with DCM. The resulting Boc-Asp(O'Bu)-Tyr(OX)-Met-Gly-Trp-Met-Asp(OtBu)-Phe-Rink amide-MBHA resin is cleaved from the resin and deblocked by shaking with a mixture of 8% phenol, 5% thioanisole, 5% water, and 3% 3,6-dioxa-1,8-octanedithiol in trifluoroacetic acid (10 mL/g resin) for 4 hours. The resin is removed by filtration, and the peptide is precipitated by addition of 10 volumes of ether. The crude peptide is purified by reversed-phase HPLC.

In another example, a cysteine-containing peptide is prepared by solid phase synthesis using the methods described above, incorporating an S-(allyloxycarbonylaminomethyl)-cysteine [Cys(allocam)] or S—(N-[2,3,5,6-tetrafluoro-4-(N'-piperidino)phenyl]-N-allyloxycarbonyl-amino)cysteine [Cys(fnam)] residue. Prior to cleavage from the resin, the cysteine residue is selectively deblocked using (Ph₃P)₄Pd and phenylsilane in DCM, then reacted with a compound of formula (3) as described above. The peptide is finally deblocked, removed from the resin, and purified as described above.

Example 21

Linker-Drug Compounds of 5-Fluorouracil

As an example of preparing compounds of the invention where D is the residue of a drug coupled through a heterocyclic N, linker-drug compounds of formula (1) may be prepared from 5-fluorouracil and a compound of formula (3) (before or after connection of the linker to a solid support) analogously to the procedures used by Taylor and Sloane, "1-Alkylcarbonyloxymethyl Prodrugs of 5-Fluorouracil (5-FU): Synthesis, Physicochemical Properties, and Topical Delivery of 5-FU", *J Pharmaceutical Sci.* 87(1): 15-20 (1998), and by Roberts and Sloane, "Synthesis of 3-Alkyl-carbonyl-oxymethyl Derivatives of 5-Fluorouracil", *J. Heterocyclic Chem.* 39: 905-910 (each incorporated herein by reference). Thus, a suspension of a compound of formula (3) wherein L is Cl (1 mmol) and NaI (1.3 mmol) in dry acetonitrile (1 mL) is stirred in the dark for 24 h, then filtered to afford a solution of the compound of formula (1) wherein L is I. The filtrate is allowed to react with a mixture of 1-(allyloxycarbonyl-oxymethyl)-5-fluorouracil [Liu, Fullwood, and Rimmer, "Synthesis of Allyloxycarbonylmethyl-5-fluorouracil and copolymerizations with N-vinylpyrrolidinone", *J. Materials Chem.* 10: 1771-7, 2000] (0.8 mmol) and 1,8-bis (dimethylamino)naphthalene at ambient temperature. After 6 h, the mixture is diluted with ether, stirred for 1 h, and filtered. The filtrate is concentrated to provide the crude protected product, which is treated with a mixture of tetrakis(triphenylphosphine)-palladium(0) and phenylsilane in anhydrous THF for 1 h to remove the allyloxycarbonylmethyl protecting group. The mixture is evaporated, and the residue is purified by silica gel chromatography to provide the linker-drug compound of formula (1) where the drug-linker moiety is ready for attachment to the solid support.

Example 22

Preparation of 6-azidohexanal

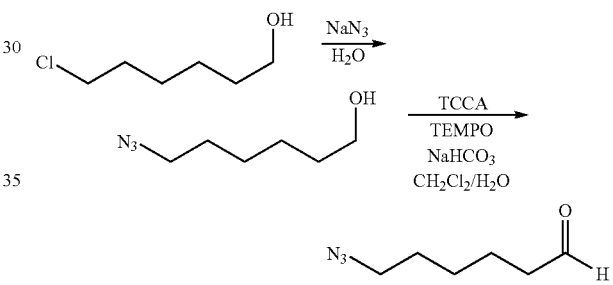

(1) 6-Azido-1-hexanol: a mixture of 6-chloro-1-hexanol (25 g, 183 mmol) and sodium azide (32.5 g, 500 mmol) in 200 mL of water was heated at reflux for 20 h, then cooled to ambient temperature and extracted 3× with ethyl acetate. The combined extracts were washed with brine, dried over MgSO₄, filtered, and concentrated to yield the product as a pale yellow oil (28.3 g).

(2) 6-Azidohexanal: Solid trichloroisocyanuric acid (TCCA; 4.3 g) was added in small portions to a vigorously stirred mixture of 6-azido-1-hexanol (7.15 g) and sodium bicarbonate (5.0 g) in dichloromethane (100 mL) and water (10 mL). The mixture was stirred for an additional 30 minutes after addition, then filtered through a pad of diatomaceous earth. The organic phase was separated and washed successively with sat. aq. NaHCO₃ and brine, then dried over MgSO₄, filtered, and concentrated to provide the product (5.8 g), which was used without further purification.

Example 23

Preparation of Azidoalcohols

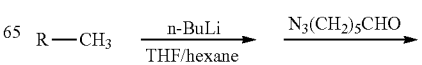

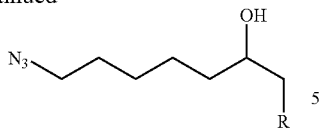

A 1.6 M solution of n-butyllithium (3.1 mL, 5.0 mmol) in hexane was added dropwise to a stirred solution of R—CH$_3$ (5.0 mmol) in anhydrous tetrahydrofuran (THF) (15 mL) cooled to −78° C. After addition, the cooling bath was removed and the mixture was allowed to warm slowly to 0° C. over approximately 30 min. The mixture was then cooled back to −78° C., and 6-azidohexanal (5.5 mmol) was added. After stirring for 15 minutes, the cooling bath was removed and the mixture was allowed to warm. At the point where the mixture became clear, 5 mL of saturated aq. NH$_4$Cl was added and the mixture was allowed to continue warming to ambient temperature. The mixture was diluted with ethyl acetate and washed successively with water and brine, and then dried over MgSO$_4$, filtered, and evaporated to provide the crude product as an oil. Chromatography on silica gel using a gradient of ethyl acetate in hexane provided the purified products.

Compounds prepared according to this method include:

1-(4-(trifluoromethyl)phenylsulfonyl)-7-azido-2-heptanol (R—CH$_3$=4-(trifluoromethyl)phenyl methyl sulfone);

1-(4-chlorophenylsulfonyl)-7-azido-2-heptanol (R—CH$_3$=4-chlorophenyl methyl sulfone);

1-(phenylsulfonyl)-7-azido-2-heptanol (R—CH$_3$=phenyl methyl sulfone);

1-(4-methylphenylsulfonyl)-7-azido-2-heptanol (R—CH$_3$=4-methylphenyl methyl sulfone);

1-(4-methoxyphenylsulfonyl)-7-azido-2-heptanol (R—CH$_3$=4-methoxyphenyl methyl sulfone);

1-(2,4,6-trimethylphenylsulfonyl)-7-azido-2-heptanol (R—CH$_3$=2,4,6-trimethylphenyl methyl sulfone);

1-(morpholinosulfonyl)-7-azido-2-heptanol (R—CH$_3$=4-(methylsulfonyl)-morpholine;

1-(methanesulfonyl)-7-azido-2-heptanol (R—CH$_3$=dimethyl sulfone);

1-cyano-7-azido-2-heptanol (R—CH$_3$=acetonitrile);

1-(morpholinocarbonyl)-7-azido-2-heptanol (R—CH$_3$=4-acetylmorpholine); and 1-(9-fluorenyl)-6-azido-1-hexanol ("R—CH$_3$"=fluorene).

Example 24

Preparation of Azido-Linker Chloroformates

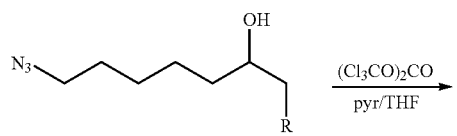

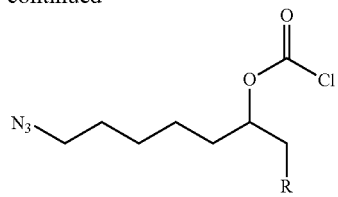

Pyridine (160 µL) was added dropwise to a stirred solution of the azidoalcohol of Example 23 (1.0 mmol) and triphosgene (500 mg) in 15 mL of anhydrous THF. The resulting suspension was stirred for 10 minutes, then filtered and concentrated to provide the crude chloroformate as an oil.

Compounds prepared according to this method include:

1-(4-(trifluoromethyl)phenylsulfonyl)-7-azido-2-heptyl chloroformate;

1-(4-chlorophenylsulfonyl)-7-azido-2-heptyl chloroformate;

1-(phenylsulfonyl)-7-azido-2-heptyl chloroformate;

1-(4-methylphenylsulfonyl)-7-azido-2-heptyl chloroformate;

1-(4-methoxyphenylsulfonyl)-7-azido-2-heptyl chloroformate;

1-(2,4,6-trimethylphenylsulfonyl)-7-azido-2-heptyl chloroformate;

1-(morpholinosulfonyl)-7-azido-2-heptyl chloroformate;

1-(methanesulfonyl)-7-azido-2-heptyl chloroformate;

1-cyano-7-azido-2-heptyl chloroformate;

1-(morpholinocarbonyl)-7-azido-2-heptyl chloroformate; and 1-(9-fluorenyl)-6-azido-1-hexyl chloroformate.

En route to a control system lacking the trigger functionality, 6-azidohexyl chloroformate was prepared as described above, starting from 6-azidohexanol. The control system cannot undergo beta-elimination.

Example 25

Preparation of Azido-Linker-HSE Carbonates

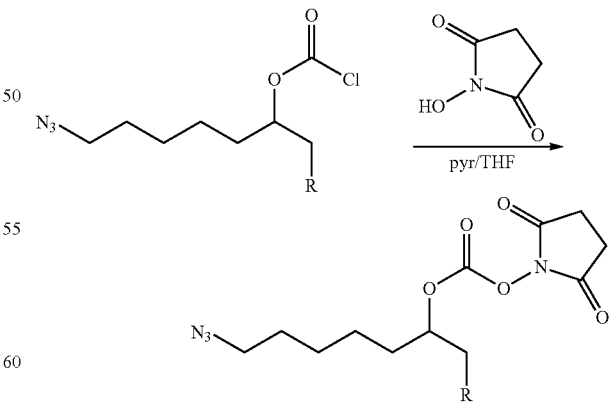

A solution of the chloroformate of Example 24 in 15 mL of dry THF was treated successively with N-hydroxysuccinimide (350 mg) and pyridine (250 µL) for 10 minutes. The mixture was then concentrated, and the residue was redissolved in ethyl acetate. After washing with 0.1 N HCl, water, sat. NaHCO₃, water, and brine, the solution was dried over MgSO₄, filtered, and evaporated. In some cases, the HSE carbonate spontaneously crystallized, and was recrystallized from ethyl acetate/hexane. In other cases, the crude HSE carbonate was first chromatographed on silica gel using a gradient of ethyl acetate in hexane, followed by crystallization. All compounds were crystalline with the exception of that obtained from 1-(methanesulfonyl)-7-azido-2-heptanol.

Compounds prepared according to this method include:

O-[1-(4-(trifluoromethyl)phenylsulfonyl)-7-azido-2-heptyl]-O'-succinimidyl carbonate;

O-[1-(4-chlorophenylsulfonyl)-7-azido-2-heptyl]-O'-succinimidyl carbonate;

O-[1-(phenylsulfonyl)-7-azido-2-heptyl]-O'-succinimidyl carbonate;

O-[1-(4-methylphenylsulfonyl)-7-azido-2-heptyl]-O'-succinimidyl carbonate;

O-[1-(4-methoxyphenylsulfonyl)-7-azido-2-heptyl]-O'-succinimidyl carbonate;

O-[1-(2,4,6-trimethylphenylsulfonyl)-7-azido-2-heptyl]-O'-succinimidyl carbonate;

O-[1-(morpholinosulfonyl)-7-azido-2-heptyl]-O'-succinimidyl carbonate;

O-[1-(methanesulfonyl)-7-azido-2-heptyl]-O'-succinimidyl carbonate;

O-[1-cyano-7-azido-2-heptyl]-O'-succinimidyl carbonate;

O-[1-(morpholinocarbonyl)-7-azido-2-heptyl]-O'-succinimidyl carbonate;

O-[1-(9-fluorenyl)-6-azido-1-hexyl]-O'-succinimidyl carbonate;

Also prepared according to this method was O-[6-azidohexyl]-O'-succinimidyl carbonate, starting from 6-azidohexyl chloroformate en route to the control system compound lacking a trigger group.

Example 26

Preparation of DBCO-SulfoNHS Ester

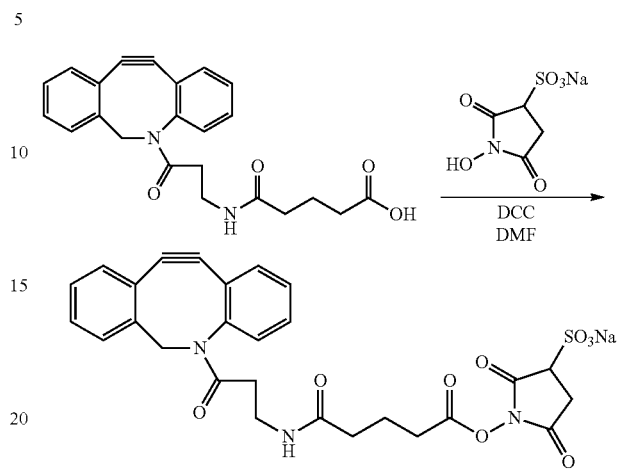

DBCO-sulfoNHS ester was prepared according to Staros, J. V., *Biochemistry* 1982, 21, 3950-3955. A solution of 0.88 M dicyclohexylcarbodiimide in DMF (250 µL) was added to a suspension of 43.4 mg sodium N-hydroxysulfosuccinimide (200 µmol; Thermo Scientific) and 78.1 mg DBCO-acid (200 µmol; Click Chemistry Tools) in 250 µL DMF in a 1.5 mL microcentrifuge tube. The mixture was incubated 16.5 hr at RT on a Daigger Vortex Genie 2 (vortex setting 3), during which time the sodium N-hydroxysulfosuccinimide dissolved and another precipitate formed. After cooling at 4° C. for 2.5 hr, the suspension was centrifuged (14,000 rpm, 10 min) and the supernatant transferred to a 50 mL centrifuge tube. The washes were pooled with the original supernatant to give a total volume of 1.3 mL. Ethyl acetate (30 mL) was added, and a precipitate was allowed to form over 1 hour. The precipitate was collected by centrifugation (4000 rpm, 10 min). The pellet was washed successively with 20 mL of ethyl acetate (2×) and 15 mL of ethyl ether (3×), then dried giving a yield of 89.1 mg (151 µmol).

Example 27

Preparation of DBCO-Agarose

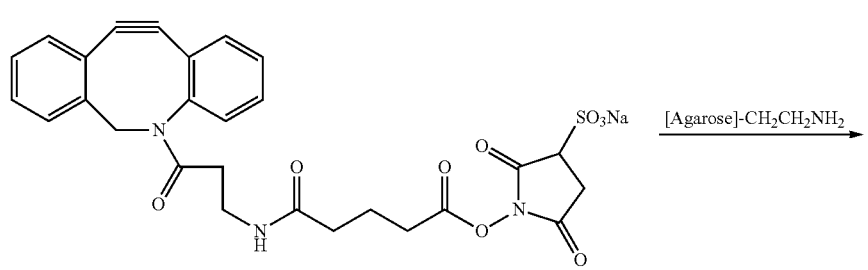

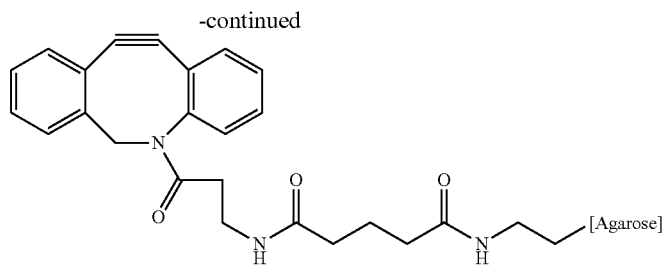

A suspension of 2 mL of aminoethyl agarose (3~6 µmol/mL; Gold Biotechnology; Very Low Density Aminoethyl Agarose, 4% crosslinked) in 3 mL of 100 mM HEPES, pH 7.5, in a 12 mL fitted column (Applied Separations) was treated with a solution of 3.54 mg (6 µmol) of DBCO-SulfoNHS ester (Example 26) in 167 µL DMF, and the mixture was agitated. Reaction progress was followed by removing 20 µL, obtained from drops released at the column outlet. The aliquot was diluted with 120 µL of water, acidified with 20 µL of 0.2 M acetic acid, pH 3.5, to remove absorbance of the NHS, and the DBCO content was determined by UV absorbance measurement. After 3.5 hrs, the measured DBCO remained constant and indicated that >90% of the DBCO had reacted. The beads were drained, and sequentially washed with 5 mL of 1 M NaCl and 4.5 mL of 0.1 M HEPES, pH 7.5. The combined washings were acidified with an equal volume of 0.2 M acetic acid, pH 3.5, and UV measurement indicated less than 4% of the initial DBCO absorbance remained, indicating a conversion of >96%. The resin (5.8 µmol of DBCO; 0.2 to 6.2 µmol of amine) was suspended in 3 mL of 0.25 M HEPES, pH 7.5, and 0.5 mL of 0.4 M acetic anhydride in acetonitrile (200 µmol) was added and agitated for 1 hr. The resin was washed with 5 mL of 0.25 M HEPES, pH 7.5, followed by 5 mL of 0.1 M HEPES, pH 7.5. The solvent was exchanged by successively washing with 2 mL each of 25%, 50%, and 75% MeOH in 0.1 M HEPES, pH 7.5, followed by 10 mL of 100% MeOH. The resin was stored in MeOH at 0-4° C.

Example 28

Preparation of Linked Fluoresceins

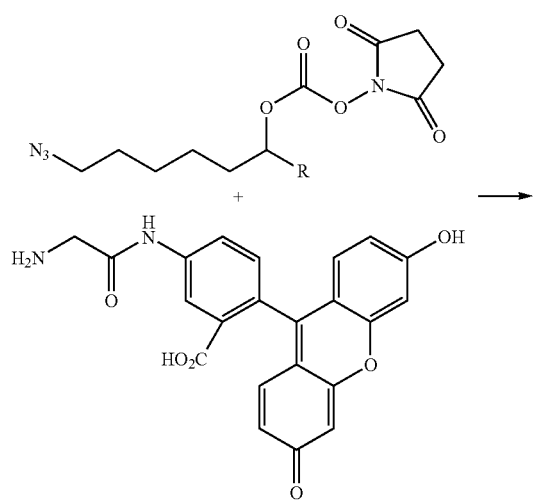

-continued

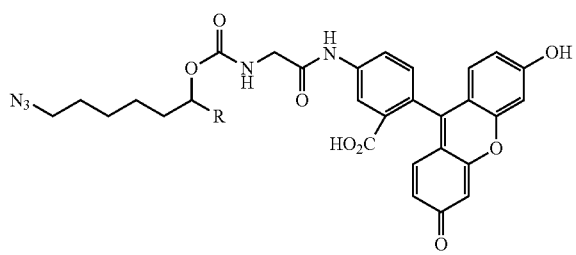

A solution of 25 mM azido-linker-HSE carbonate (Example 25) in DMSO (100 µL) was added to a 10 mg/mL solution of 5-(aminoacetamido)fluorescein (Invitrogen) in DMSO (115 µL). After 1 h at ambient temperature, the mixture was analyzed by reversed-phase HPLC, indicating complete consumption of azido-linker-HSE carbonate and formation of a single linked fluorescein product. The solutions were used without purification.

Compounds prepared according to this method include R=phenyl-SO$_2$CH$_2$; R=(4-chlorophenyl)-SO$_2$CH$_2$; and R=H (control system).

Example 29

Preparation of Fluorescein-Agarose Conjugates

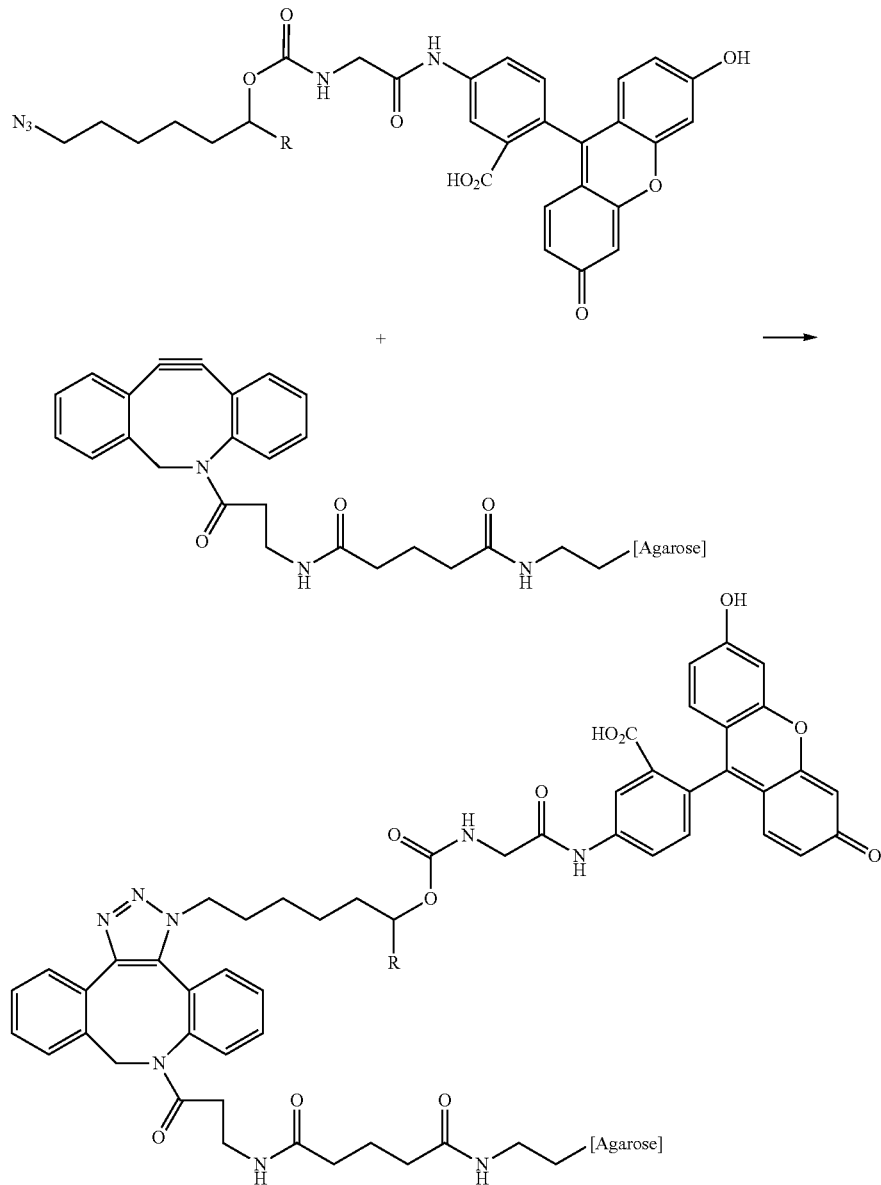

The solution of linked fluorescein of Example 28 (2.5 mop was added to a suspension of 0.3 mL of the packed DBCO-agarose of Example 27 (1.15 μmol) suspended in 0.7 mL MeOH in a 1.5 mL centrifuge tube. The mixture was agitated for 20 hr using a vortex mixer, centrifuged (2 min, 4K rpm), and washed 10× with 1 mL of MeOH until the absorbance at 492 nm of the wash was <0.001. The absorbance of the combined washes was used to estimate the amount of conjugation to agarose, based on unreacted linked fluorescein.

Using this method, conjugates were prepared having linkers comprising R=phenyl-$SO_2$—$CH_2$ (1.17 μmol of fluorescein conjugated); R=(4-chlorophenyl)-$SO_2$—$CH_2$ (0.46 μmol of fluorescein conjugated); and R=H (0.92 μmol of fluorescein conjugated).

Example 30

Release of Fluorescein from Fluorescein-Agarose Conjugates

The fluorescein-agarose conjugate of Example 29 (15 μL; calculated to have 57 nmol fluorescein conjugate; measured as packed volume in a centrifuge tube) was suspended in 1 mL of 0.1 M bicine, pH 8.5, in a 1.5 mL microfuge tube and agitated on a rotating rocker (Clay-Adams Nutator) in a 37° C. incubator. At appropriate intervals the suspension was centrifuged, the absorbance at 495 nm of the supernatant determined, and the supernatant returned to the vessel. After ~7 days, the volume was about 650 μL, presumably due to evaporation. To obtain an estimate of the absorbance at infinite time, the measured absorbacne was corrected to the starting volume of 1.0 mL.

When R=phenyl-$SO_2$—$CH_2$, 57 nmol of fluorescien conjugate was reacted, the total amount of fluorescein released was 29.9 nmol, and the release of fluorescein showed k=0.0488 hr$^{-1}$ ($t_{1/2}$=14.2 hours). When R=(4-chlorophenyl-$SO_2$—$CH_2$), 15 nmol fluorescein conjugate was allowed to react for 116 hr; the released absorbance indicated k=0.0821 h$^{-1}$ ($t_{1/2}$=8.4 hr), and the total fluorescein released was 21 nmol (each measurement was within experimental error). When R=H, 31 nmol of fluorescein conjugate was allowed to react for 140 hr, no absorbance was released; thus, k=<0.0001 hr$^{-1}$ ($t_{1/2}$>5,000 hr).

Example 31

Preparation of PEGA-DBCO

PEGA, a beaded copolymer of polyethylene glycol and dimethylacrylamide, was derivatized with DBCO as follows. To a suspension of 1 mL of Amino PEGA resin (Merck; 0.41 μmol amino/g dry weight; 12 mL/g in $H_2O$, 10 mL/g in MeOH) in 1 mL of 100 mM HEPES, pH 7.5 (30.7 μmol total amines) in a 3-mL fritted column, was added 24.2 mg (41 μmol) of DBCO-SulfoNHS ester (Example 26) in 405 μL of 100 mM HEPES, pH 7.5. The mixture was agitated by constant end-over-end turning on a Hematology/Chemistry Mixer (Fisher). As the reaction progressed, a 10 μL aliquot obtained from drops released at the outlet was diluted with 760 μL of $H_2O$, acidified with 30 μL of 0.2 M acetic acid, pH 3.5, to remove absorbance of the NHS, and used to determine remaining soluble DBCO by UV measurements (the unused portion of the aliquot was returned to the reaction). After 4 hrs, the amount of soluble DBCO remained constant. The resin was sequentially washed with 4 mL of 0.1 M HEPES, pH 7.5, 2.5 mL of 1 M NaCl, and 2.5 mL of 0.1 M HEPES, pH 7.5. The combined washings were acidified with an equal volume of 0.2 M acetic acid, pH 3.5, and UV measurement indicated 30 μmol of the initial DBCO absorbance was bound to the resin. The resin was equilibrated with 1:1 MeOH/0.1 M HEPES, pH 7.5, converted to a 2 mL slurry, treated with 0.6 mL of 61.5 mM acetyl-N-hydroxysuccinimide in 1:1 MeOH/ 0.1 M HEPES, pH 7.5 (36.9 μmol) and agitated for 2 h. The resin was washed with 5 mL of 0.25 M HEPES, pH 7.5, followed by 5 mL of 0.1 M HEPES, pH 7.5. The solvent was exchanged by successively washing with 3 mL each of 25%, 50%, and 75% methanol in 0.1 M HEPES, pH 7.5, followed by 10 mL of methanol. The resin was stored in methanol at 0-4° C. The final yield was 30 μmol in 750 μL packed volume.

Example 32

Preparation of PEGA-Fluorescein Conjugates

An aliquot of PEGA-DBCO (Example 31) in methanol (35-50 μL packed resin; about 1.15-1.7 μmol DBCO) was suspended in 0.7 mL of methanol in a 1-mL fritted column. A solution of linked fluorescein (Example 28; 2.5 μmol) in 215 μL of DMSO was added, and the mixture was agitated for 16 hr by end-over-end turning on a Hematology/Chemistry Mixer (Fisher). The resulting resin was washed with methanol (7.5-10 mL) to remove unbound fluorescein; the combined washes were analyzed for fluorescein content by measurement of the absorbance at 492 nm after dilution into 0.1 M sodium borate. Bound fluorescein was determined by the difference between the total fluorescein adding in the reaction and the unbound measured after resin washing. The column was drained of excess methanol, and the wet resin was stored at 4° C.

Conjugates prepared according to this procedure include: R=phenyl-$SO_2CH_2$ (containing 1.14 μmol of fluorescein/μL packed resin); R=(4-chlorophenyl)-$SO_2CH_2$ (containing 0.68 μmol of fluorescein/μL packed resin); and control R=H (containing 1.12 μmol of fluorescein/μL packed resin).

Example 33

Release of Fluorescein from PEGA-Fluorescein Conjugates

Figure 4:
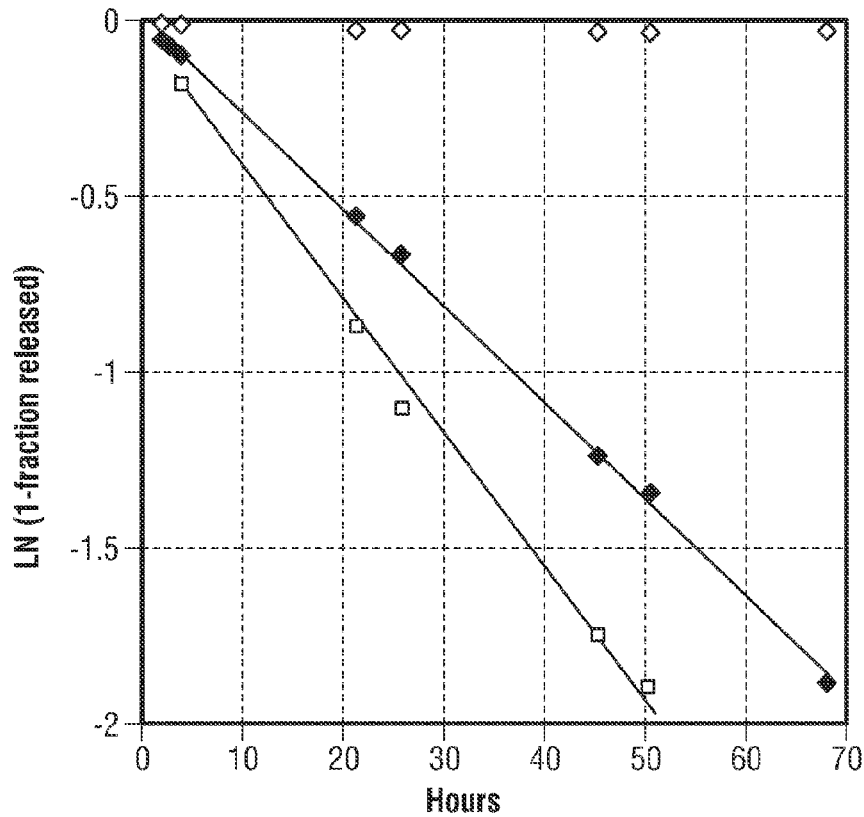
FIG. 4 shows the results of Example 33 as a comparison of rates of release at 37° C., pH 8.4. Open squares: 4-chlorophenylsulfonyl analog (k=0.040/h; $t_{1/2}$=17 h); solid diamonds: phenylsulfonyl analog (k=0.027/h; $t_{1/2}$=26 h); open diamonds: control, non-releasable linker (no release observed; k<0.00001/h; $t_{1/2}$>6900 h).
Figure 5:
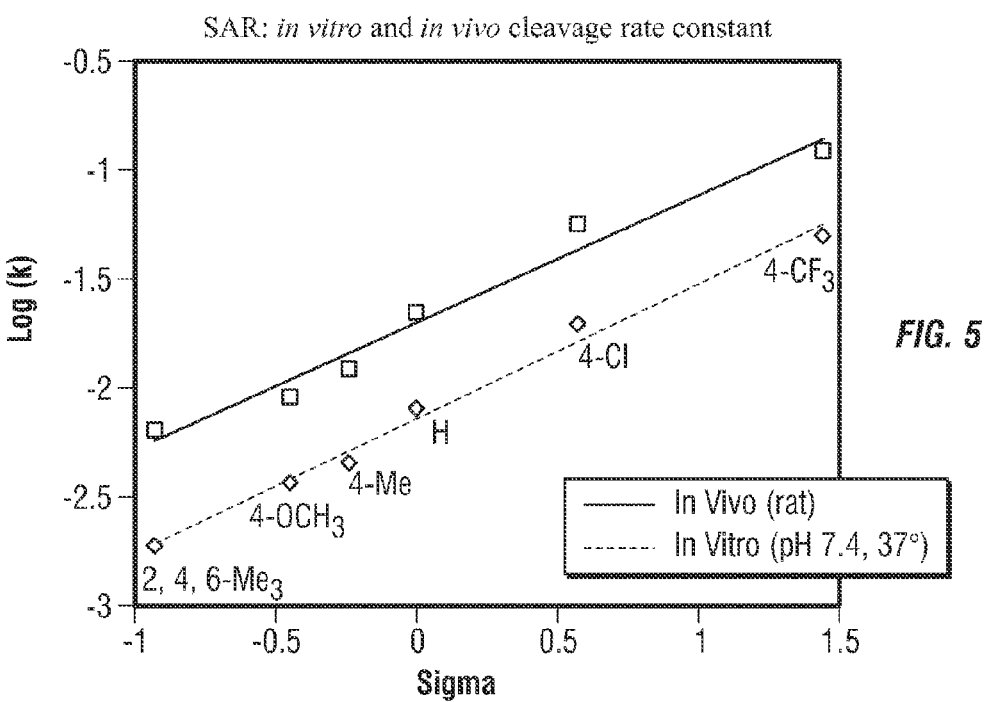
FIG. 5 shows a comparison of in vivo and in vitro release rates of drugs as a function of the Hammett constants associated with the trigger on a series of PEG-conjugated linkers wherein R1 is optionally substituted phenyl SO2, R2 is H and the drug is fluorescein. In accordance with theory, the rate of beta-elimination from the linker is dependent on the phenyl substituent, with electron-withdrawing substituents (positive sigma: CF3, Cl) giving faster rates and electron-donating substituents (negative sigma: Me, OMe) giving slower rates. The rate correlation is observed both in vitro and in vivo (measured in rat).

The conjugate of Example 32 (20-30 nmol of total fluorescein) was suspended in 1 mL of 0.1 M bicine, pH 8.45, 37° C., in a 1.5 mL microfuge tube and agitated on a rotating rocker (Clay-Adams Nutator) in a 37° C. incubator. At intervals the suspension was centrifuged, the optical density at 492 nm of the supernatant was determined, and the supernatant returned to the vessel. After 68 hours, the incubation temperature was increased to 67° C., and incubation was continued for an additional 3.5 hours to allow determination of complete hydrolysis for the two samples with releasable linkers (R=phenyl-$SO_2CH_2$ and (4-chlorophenyl)-$SO_2CH_2$) and to allow estimation of an upper limit of rate of cleavage of the sample with a non-releasable linker (R=H). Data is shown in FIG. 4.

The conjugate having R=phenyl-$SO_2CH_2$ (~22.8 μmol of bound fluorescein) released 23 μmol of fluorescein with k=0.027/h ($T_{1/2}$=26 h), while the conjugate having R (4-chlorophenyl)-$SO_2CH_2$ (~27.2 μmol of bound fluorescein) released 29 μmol of fluorescein with k=0.040/h ($T_{1/2}$=17 h). These calculations for bound versus released fluorescein are within experimental error. An upper limit for the rate of release from the non-releasable conjugate (model system) having R=H (34.6 μmol of bound fluorescein) of k<0.0001/h ($T_{1/2}$>6900 h) was estimated, based on release of <2 μmol of fluorescein.

Example 34

Modified Metal Surfaces

Metal surfaces modified with amine, carboxylate, azide, alkyne, thiol, or maleimide groups are prepared as follows.

Amine-modified titanium surfaces are prepared according to the procedure of Xiao, et al., *Langmuir* 14: 5507-5516 (1998). Thus, a titanium surface is pretreated using water vapor plasma using a plasma cleaner/sterilizer such as a PDC-32G (Harrick, N.Y.) at 0.42 mbar for 2 minutes, then vacuum dried. The dried surface is treated with a 1% (w/v) solution of (3-aminopropyl)triethoxysilane in toluene for 48 h at 80° C. The surface is then ultrasonically washed five times using chloroform, twice with acetone, and five times with methanol, then rinsed with water and vacuum dried and cured at 100° C. for 1 h under $N_2$.

The amine-modified titanium surface is used to make the carboxylate-modified surface by treatment with a cyclic anhydride, for example succinic anhydride or glutaric anhydride. Thus, the amine-modified titanium surface is suspended in a solution of 0.1 M succinic anhydride in acetonitrile, and triethylamine is added to a final concentration of 0.1 M. After 12 h, the titanium surface is removed and washed and dried as described above.

The amine-modified titanium surface is used to make the azide-, alkyne-, and maleimide-modified surfaces by reaction with the appropriate N-hydroxysuccinimide ester of an azide-, alkyne-, or maleimide-substituted carboxylic acid, for example N-(6-azidohexanoyloxy)succinimide, N-(4-azidobutanoyloxy)-succinimide, N-(5-hexynoyloxy)succinimide, N-(3-(maleimido)propanoyloxy)-succinimide, and similar reagents. Thus, an amine-modified titanium surface is suspended in a solution of 0.1 M N-(6-azidohexanoyloxy) succinimide in acetonitrile, and triethylamine is added to a final concentration of 0.1 M. After 1 h, the titanium surface is removed and washed and dried as described above to provide an azide-modified titanium surface. Similarly, an amine-modified titanium surface is suspended in a solution of 0.1 M N-(3-(maleimido)propanoyloxy)succinimide in acetonitrile, and triethylamine is added to a final concentration of 0.1 M. After 1 h, the titanium surface is removed and washed and dried as described above to provide a maleimide-modified titanium surface.

The amine-modified titanium surface is used to make the thiol-modified titanium surface by reaction with the NHS ester of an appropriate blocked-thiol reagent. For example, an amine-modified titanium surface is suspended in a solution of 0.1 M N-(3-(2-pyridyldithio)propionyloxy)succinimide in the presence of 0.1 M triethylamine. After 1 h, the titanium surface is removed and washed and dried as described above to provide a 2-pyridyldithio-modified titanium surface. Prior to use, the 2-pyridyldithio-modified titanium surface is suspended in a 10 mM solution of tris(2-carboxyethyl)phosphine hydrochloride in 0.1 M MES buffer, pH 6. The solution is analyzed for formation of 2-pyridylthione by monitoring the absorbance at 343 nm. When the absorbance reaches a maximum, the titanium surface is washed and dried as described above to provide a thiol-modified titanium surface.

Similarly modified surfaces are prepared starting with other metals having free surface hydroxyl groups, for example stainless steel, cobalt-chrome alloys, and cobalt-chromium-molybdenum alloys.

Example 35

Modified Collagen

Collagen is treated to introduce functional groups as follows. Insoluble Type I collagen is prepared following the procedure of Tiller, et al., *Biotechnol. Bioengineering* (2001) 73:246-252. Thus, the collagen is soaked overnight in 0.5 M acetic acid at 4° C., then homogenized in a cold blender and filtered. The collagen is suspended at 1% in 0.1 M phosphate buffer, pH 7.4, and placed under vacuum to remove entrapped air bubbles.

To produce collagen modified by 2-pyridyldithio groups, the above suspension is treated with an 0.1 M solution of sulfosuccinimidyl 6-(3'-[2-pyridyldithio]-propionamido) hexanoate (Thermo Scientific) in pH 7.4 buffer for 4 h at ambient temperature, maintaining the pH at 7.4 as necessary by addition of 1 M NaOH. The resulting mixture is dialyzed to remove excess reagents.

In a similar fashion, collagen modified by azide, alkyne, or maleimide groups is prepared by treatment with the corresponding sulfosuccinimidyl reagent.

The above-described modified collagens are made into collagen films by dilution with 0.5 M acetic acid to 2.5 mg/mL, applying one mL of this to a petri dish and allowing it to dry thoroughly to form a transparent film. The films are washed with 10 mM phosphate buffer, pH 7.4, for 3 h, then with water for 2 h, and dried. Alternatively, films made from underivatized collagen may be treated as described above to introduce the various functional groups.

Example 36

Modified Hydrogels

Hydrogels are cross-linked polymer gels, such as calcium alginate, sodium polyacrylate, polyvinyl alcohol, polyacrylamide, polyethyleneoxide, and polyvinyl pyrrolidone, consisting of a network of polymer chains that are water-insoluble, sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. They may be shaped into sheets to provide and maintain a moist wound environment conducing to maximal healing. By increasing moisture content, hydrogels have the ability to help clean and debride necrotic tissue. Hydrogels are non-adherent and can be removed without trauma to the wound. Various hydrogel dressings are commercially available as sheets, for example calcium alginate prepared as a textile fiber called TegaGel® (3M) and sodium polyacrylate called AQUASORB® (DeRoyal).

Alginate- and polyacrylate-based hydrogels may be modified through derivitization of free carboxylate groups using a carbodiimide condensing reagent, for example EDCI, in the presence of N-hydroxysuccinimide to provide alginate comprising activated N-hydroxysuccinimide esters. The activated alginate is then coupled with an amine compound that also comprises the desired functional group, for example azide, amine, alkyne, 2-pyridyldithiol, or maleimide.

Example 37

Modified Cellulosic Materials

Cellulosic materials, such as cotton, surgical gauzes, surgical sutures, absorbent pads, bandages, burn dressings, and packings for tooth cavities in the form of cotton, paper. Fabrics, sponges, and the like, which contain free hydroxyl groups may be modified in various ways.

In one method, the material is treated with a polymaleic anhydride or a poly(maleic anhydride-co-vinyl acetate) to introduce carboxylate functional groups. The copolymer is prepared by radical copolymerization of maleic anhydride and vinyl acetate as described in Xiao, et al., "Synthesis and properties of starch-g-poly(maleic anhydride-co-vinyl acetate)," *Express Polymer Letters* 4:9-16 (2001). Thus, a mixture of the cellulosic material and copolymer in water is heated to 100° C. to drive off the water. The resulting material is washed thoroughly with ethanol and dried to provide carboxylate-modified cellulosic material.

The resulting carboxylated cellulosic material is activated by reaction with a carbodiimide condensing reagent, for example EDCI, in the presence of N-hydroxysuccinimide to provide modified cellulose comprising activated N-hydroxysuccinimide esters. The activated cellulose is then coupled with an amine compound that also comprises the desired functional group, for example azide, amine, alkyne, 2-pyridyldithiol, or maleimide. Thus, to prepare an alkyne-modified cellulosic material, the activated cellulosic material would be reacted with an alkynylamine, for examine 5-hexyn-1-amine.

Example 38

SN-38 Releasably Attached to a Titanium Surface Via Alkyne-Azide Cycloaddition

An alkyne-modified titanium surface prepared as described in Example 34 is suspended in a 0.1 M solution of the linker-SN-38 compound of Example 13 in tetrahydrofuran. A catalyst mixture comprising 50 mM $CuSO_4$, 50 mM tris-[(1-benzyl-1H-1,2,3-triazol-4-yl)methyl]amine (TBTA) and 100 mM sodium ascorbate is added, and the reaction is allowed to proceed for 48 h. The titanium surface is removed, ultrasonically washed five times using chloroform, twice with acetone, and five times with methanol, then rinsed with water and vacuum dried and cured at 100° C. for 1 h under $N_2$.

Example 39

Antibody Releasably Attached to a Modified Collagen

The antibody is activated on a surface amine group by reaction with a releasable linker comprising an azido group and an N-hydroxysuccinimidyl carbonate prepared as described in co-pending application published as WO2009/158668 and as described above. Thus, a solution of the antibody at 2 mg/mL of 0.1 M $NaHCO_3$, pH 8.4, is treated with a solution of the azide-linker-NHS in DMSO for 4 hrs at ambient temperature. The resulting mixture is dialyzed against PBS, pH 7.4, to remove excess reagents and provide a solution of the antibody attached to the azide-linker via a carbamate group.

An alkyne-modified collagen prepared as described in Example 35 is suspended in a solution of the azide linker-antibody compound in PBS. A catalyst mixture comprising 50 mM $CuSO_4$, 50 mM tris-[(1-benzyl-1H-1,2,3-triazol-4-yl)methyl]amine (TBTA) and 100 mM sodium ascorbate is added, and the reaction is allowed to proceed for 48 h. The collagen is removed and washed thoroughly with water to provide the antibody releasably attached to collagen.

Example 40

Growth Factor Releasably Attached to Surgical Gauze

Growth factors or cytokines may be releasably attached to solid supports such as metal surfaces, collagens, hydrogels, and cellulosic materials. For example, a growth factor, such as platelet-derived growth factor (PDGF), may be releasably attached to surgical gauze to promote wound healing.

The growth factor is activated on a surface amine group by reaction with a releasable linker comprising an azido group and an N-hydroxysuccinimidyl carbonate prepared as described in co-pending application published as WO2009/158668, and as described above. Thus, a solution of the growth factor at 2 mg/mL of 0.1 M $NaHCO_3$, pH 8.4, is treated with a solution of the azide-linker-NHS in DMSO for 4 hrs at ambient temperature. The resulting mixture is dialyzed against PBS, pH 7.4, to remove excess reagents and provide a solution of the growth factor attached to the azide-linker via a carbamate group.

An alkyne-modified surgical gauze prepared as described in Example 37 is suspended in a solution of the azide linker-growth factor compound in PBS. A catalyst mixture comprising 50 mM $CuSO_4$, 50 mM tris-[(1-benzyl-1H-1,2,3-triazol-4-yl)methyl]amine (TBTA) and 100 mM sodium ascorbate is added, and the reaction is allowed to proceed for 48 h. The collagen is removed and washed thoroughly with water to provide the growth factor releasably attached to surgical gauze.

Example 41

Preparation of Polymer-Coated Stent

A polymer-coated stent is prepared by a modification of the procedure described in WO2006/102247.

Primer Layer

Poly(ethylene-co-vinyl alcohol) (EVAL) is dissolved in 1:1 DMSO:DMAC to give a 2% by weight solution. The 2% solution of the polymer is applied to a 13 mm TETRA® stent in a series of 10-second passes, to deposit 10 µg of coating per spray pass. Between the spray passes, the stent is dried for 10 seconds using a flow of air at 80° C. Five spray passes are applied to form a 50 µg primer layer, followed by baking the primer layer at 140° C. for one hour.

Drug-Containing Layer

The hydroxyl groups of EVAL are activated with carbonyldiimidazole and reacted with $PEG-NH_2$ to give a PEG-EVAL conjugate linked by a urethane moiety. Similarly, the precursor compound of the invention is coupled to the activated hydroxyl groups in a separate reaction. These may be reacted with propargyl bromide and triethylamine in DMF solution to provide a PEG-EVAL conjugate containing a terminal alkyne. The alkyne is reacted with the intermediate containing an azidoalkyl group in $R^1$, $R^2$, $R^5$ or B. Drug may be coupled before or after this reaction.

This polymer is dissolved in a 1:1 DMSO:DMAC to give a 2% by weight solution. The same apparatus used to spray the primer layer on the stent is used to apply the drug layer. Seventy spray passes are performed to form a 700 µg drug-polymer layer, followed by drying the drug-polymer layer at 50° C. for 2 hours.

Topcoat Layer

A topcoat layer comprising 2% by weight solution of poly (ethylene-co-butyl vinyl ether-co-vinyl alcohol) in 4:1 DMAC:pentane is applied over the drug-containing layer using the same apparatus. Fifteen spray passes are performed to form a 150 µg topcoat layer, followed by drying at 50° C. for 2 hours.

Finish Coat Layer

A finish coat layer comprising 2% by weight of poly(ethylene-co-mPEG(560)urethane-co-vinyl alcohol) in a 5:3:2 solution of DMAC:ethanol:DMSO is applied in a manner identical to the application of the previous layers. Thirty-five spray passes are performed to form a 350 µg finishing coat layer, followed by drying at 50° C. for 2 hours.

Example 42

Nitinol (TiNi) Drug Conjugate

Nitinol (TiNi) is thin-coated with DLC using 13.56 MHz RF plasma-assisted chemical vapor deposition (PACVD). The DLC layers are deposited under a bias voltage of 400 V and deposition pressure of 1.33 Pa. The surface of TiNi-DLC is treated to remove impurities and the samples are vacuum-dried for 24 h to obtain an oxidized TiNi-DLC. Shin, et al., *J. Bioactive Compatible Polymers* (2009) 24:316-328.

Alkynyl PEG is isocyanated by a modification of known procedures. Id. Alkynyl PEG is reacted with 0.2% dibutyltin dilaurate (DBTDL) and hexamethylene diisocyanate (HDI) (2 eq.) dissolved in toluene under nitrogen at 45° C. for 45 min.

The TiNi-DLC samples are grafted with alkynyl-PEG isocyanate and stannous octoate in toluene at 40° C. for 24 h to produce PEG-grafted TiNi-DLC. The TiNi-DLC-PEG is reacted with a conjugate containing an azidoalkyl linker, via Huisgen's 1,3-dipolar cycloaddition catalyzed by copper sulfate. Drug may be coupled before or after this reaction.

Example 43

Medicated Gauze

Surgical gauze (cotton made, 5 cm×5 cm) is reacted with polymaleic anhydride dissolved in acetone at a concentration of about 10% by weight, optionally containing catalytic hydrochloric acid, and the mixture is reacted for 10 hours at 25° C., as generally described in U.S. Pat. No. 4,265,233.

The polymer-impregnated gauze is reacted with N-hydroxysuccinimide (NHS) and DCC in DMF for 3 hours at 25° C. The NHS-activated acid is reacted with the intermediate compound containing an amine linker. Drug may be coupled before or after this reaction.

Example 44

Collagen Drug Conjugates

Dermal bovine collagen (DBC) is thiolated by reaction with γ-thiobutyrolactone in DMSO. Kurimoto, et al., *Journal of Biotechnology* (2001) 86:1-8. Alternatively, DBC is thiolated using a disulfide-containing reagent prepared by reacting N,N'-disuccinoylcystamine with 1,1'-carbonyldiimidazole followed by reduction of the disulfide groups with 1,4-dithiothreitol. Nicolas & Gagnieu, *Biomaterials* (1997) 18:807-813.

The thiolated DBC is reacted with carbonyldiimidazole and triethylamine in DMF, followed by reaction with an intermediate containing an amine in the $R^1$, $R^2$, $R^5$ or B functional group to provide a thiocarbamate-linked collagen conjugate. Drug may be coupled before or after this reaction.

In other embodiments, the thiolated DBC is reacted with NHS-activated 3-butynoic acid in DMF. The alkyne containing product is further reacted with a drug conjugate containing an azidoalkyl linker, via Huisgen's 1,3-dipolar cycloaddition catalyzed by copper sulfate.

Example 45

Coated Biomedical Devices (Pacemaker, Heart Valves, Stents)

The surface of the medical device is grafted with a vinyl containing polymer, such as a hydroxy-functional PVP copolymer (e.g., as described in U.S. Pat. No. 3,563,968), using ceric ion initiation (CeIV), ozone exposure or UV irradiation, as generally disclosed in U.S. Pat. No. 6,033,719.

The hydroxyl groups of the polymer are reacted with reacted with carbonyldiimidazole, followed by reaction with an intermediate containing an amine in $R^1$, $R^2$, $R^5$ or B to provide a carbamate-linked conjugate. Drug may be coupled before or after this reaction.

The invention claimed is:
1. A composition of the formula

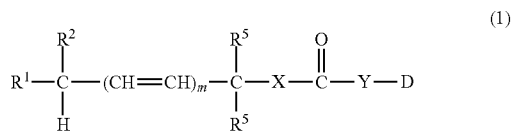

wherein m=0 or 1;
at least one or both $R^1$ and $R^2$ is independently CN; $NO_2$; optionally substituted aryl; optionally substituted heteroaryl; optionally substituted alkenyl; optionally substituted alkynyl; $COR^3$ or $SOR^3$ or $SO_2R^3$ wherein $R^3$ is H or optionally substituted alkyl; aryl or arylalkyl, each optionally substituted; heteroaryl or heteroarylalkyl, each optionally substituted; or $OR^9$ or $N(R^9)_2$ wherein each $R^9$ is independently H or optionally substituted alkyl, or both $R^9$ groups taken together with the nitrogen to which they are attached form a heterocyclic ring; or $SR^4$ wherein $R^4$ is optionally substituted alkyl; aryl or arylalkyl, each optionally substituted; or heteroaryl or heteroarylalkyl, each optionally substituted; wherein $R^1$ and $R^2$ are joined to form a 3-8 membered ring; and wherein one and only one of $R^1$ and $R^2$ is H or is alkyl, arylalkyl or heteroarylalkyl, each optionally substituted; each $R^5$ is independently H or is alkyl, alkenylalkyl, alkynylalkyl, aryl, arylalkyl, heteroaryl or heteroarylalkyl, each optionally substituted; D is a residue of a drug or prodrug coupled through O, S, or N; Y is absent and X is O or S; or Y is $NBCH_2$ and X is O; wherein B is alkyl, aryl, arylalkyl, heteroaryl or heteroarylalkyl, each optionally substituted; and wherein one of $R^1$, $R^2$, $R^5$ or B is coupled to a solid support.

2. The composition of claim 1 wherein the solid support is a stent, a hydrogel, a catheter, a wound dressing, an implant, a plaster, an orthopedic device, or a dental prosthesis.

3. The composition of claim 1 wherein said solid support is further coupled to a protective inert polymer.

4. A composition of the formula

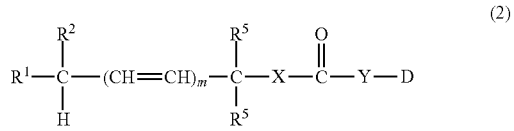

wherein m=0 or 1;
at least one or both $R^1$ and $R^2$ is independently CN; $NO_2$; optionally substituted aryl; optionally substituted heteroaryl; optionally substituted alkenyl; optionally substituted alkynyl; $COR^3$ or $SOR^3$ or $SO_2R^3$ wherein $R^3$ is H or optionally substituted alkyl; aryl or arylalkyl, each optionally substituted; heteroaryl or heteroarylalkyl, each optionally substituted; or $OR^9$ or $N(R^9)_2$ wherein each $R^9$ is independently H or optionally substituted alkyl, or both $R^9$ groups taken together with the nitrogen to which they are attached form a heterocyclic ring; or $SR^4$ wherein $R^4$ is optionally substituted alkyl; aryl or arylalkyl, each optionally substituted; or heteroaryl or heteroarylalkyl, each optionally substituted; wherein $R^1$ and $R^2$ are joined to form a 3-8 membered ring; and wherein one and only one of $R^1$ and $R^2$ is H or is alkyl, arylalkyl or heteroarylalkyl, each optionally substituted;

each $R^5$ is independently H or is alkyl, alkenylalkyl, alkynylalkyl, aryl, arylalkyl, heteroaryl or heteroarylalkyl, each optionally substituted; D is a residue of a drug or prodrug coupled through O, S, or N; Y is absent and X is O or S; or Y is NBCH$_2$ and X is O; wherein B is alkyl, aryl, arylalkyl, heteroaryl or heteroarylalkyl, each optionally substituted; and wherein said coupling is through any of $R^1$, $R^2$, $R^5$ or B.

5. The solid support of claim 4 which is a stent, a hydrogel, a catheter, a wound dressing, an implant, a plaster, an orthopedic device, or a dental prosthesis.

6. The solid support of claim 4 which further comprises a multiplicity of coupled inert protective polymers.

7. The solid support of claim 6 wherein the protective polymer is polyethylene glycol (PEG).

8. The solid support of claim 4 wherein the drug is a peptide, a nucleic acid or a small molecule.

9. The solid support of claim 4 wherein one of $R^1$ and $R^2$ is CN.

10. The solid support of claim 4 wherein at least of one $R^1$ and $R^2$ comprises phenyl or phenylene.

11. The solid support of claim 4 wherein one of $R^1$ and $R^2$ is SO$_2$R$^3$ and the other is H, alkyl or phenyl.

12. The solid support of claim 4 wherein m is 0.

13. A method to prepare a solid support of claim 4 which method comprises providing a compound of formula (3)

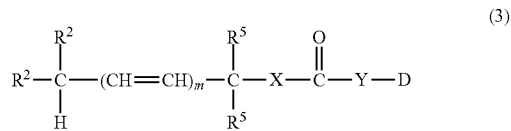

wherein m, $R^1$, $R^2$, $R^5$, X, Y, m and D are as defined in formula (1) or (2); and wherein one of $R^1$, $R^2$, $R^5$ and B comprises a functional group that couples formula (3) to a solid support, to react with the solid support under conditions whereby said solid support is coupled to said compound.

14. The solid support of claim 4 wherein $R^1$ is phenylsulfonyl, substituted phenylsulfonyl, methanesulfonyl, $(R^9)_2$N—SO$_2$, or CN; and $R^2$ is H; or $R^1$ and $R^2$ taken together with the CH to which they are attached form 9-fluorenyl.

15. The solid support of claim 4 wherein m is 0; $R^1$ is phenylsulfonyl, substituted phenylsulfonyl, methanesulfonyl, $(R^9)_2$N—SO$_2$, or CN; $R^2$ is H; one $R^5$ is optionally substituted alkyl and the other $R^5$ is H; and B is phenyl or substituted phenyl; and wherein one of $R^1$, $R^5$, and B further comprises a connection to the solid support.

16. A drug-solid support conjugate, wherein the drug is connected to the solid support via a linker; the drug molecule is attached to the linker through O, S, or N of formula (1), (2), or (3); and the drug is released from the conjugate under physiological conditions through a beta-elimination reaction.

* * * * *